United States Patent
Takahashi

(10) Patent No.: US 9,417,523 B2
(45) Date of Patent: Aug. 16, 2016

(54) PATTERN FORMING METHOD, ACTINIC RAY-SENSITIVE OR RADIATION-SENSITIVE COMPOSITION USED THEREIN, RESIST FILM, MANUFACTURING METHOD OF ELECTRONIC DEVICE USING THE SAME, AND ELECTRONIC DEVICE

(71) Applicant: FUJIFILM Corporation, Tokyo (JP)

(72) Inventor: Hidenori Takahashi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/497,462

(22) Filed: Sep. 26, 2014

(65) Prior Publication Data

US 2015/0010858 A1   Jan. 8, 2015

Related U.S. Application Data

(63) Continuation of application No. PCT/JP2013/060138, filed on Mar. 27, 2013.

(30) Foreign Application Priority Data

Mar. 27, 2012 (JP) ................. 2012-072541

(51) Int. Cl.
| | |
|---|---|
| *G03F 7/004* | (2006.01) |
| *G03F 7/038* | (2006.01) |
| *C07C 217/18* | (2006.01) |
| *G03F 7/039* | (2006.01) |
| *G03F 7/32* | (2006.01) |

(52) U.S. Cl.
CPC .............. *G03F 7/038* (2013.01); *C07C 217/18* (2013.01); *G03F 7/0392* (2013.01); *G03F 7/325* (2013.01)

(58) Field of Classification Search
CPC ........... G03F 7/0038; G03F 7/32; G03F 7/40; C07C 217/18
USPC .............. 430/270.1, 322, 325, 329, 434, 435, 430/331; 568/632, 635
See application file for complete search history.

(56) References Cited

U.S. PATENT DOCUMENTS

| | | | | |
|---|---|---|---|---|
| 5,143,784 | A * | 9/1992 | Mita .............. | 428/336 |
| 5,439,989 | A * | 8/1995 | Morton et al. ................ | 525/502 |
| 5,840,814 | A * | 11/1998 | Majoros et al. .............. | 525/502 |
| 7,993,812 | B2 * | 8/2011 | Bozano et al. ............. | 430/270.1 |
| 8,748,078 | B2 * | 6/2014 | Hayashi et al. ............. | 430/270.1 |
| 8,883,937 | B2 * | 11/2014 | Echigo et al. ................. | 525/502 |
| 2006/0127798 | A1 * | 6/2006 | Ochiai et al. ............... | 430/270.1 |
| 2010/0047709 | A1 | 2/2010 | Echigo et al. | |
| 2011/0159252 | A1 | 6/2011 | Ober et al. | |
| 2012/0100481 | A1 | 4/2012 | Ito et al. | |
| 2012/0107749 | A1 * | 5/2012 | Tono et al. .................... | 430/325 |
| 2012/0171379 | A1 | 7/2012 | Echigo et al. | |
| 2013/0004894 | A1 * | 1/2013 | Hayashi et al. ............ | 430/281.1 |
| 2013/0078569 | A1 | 3/2013 | Jain et al. | |
| 2013/0202999 | A1 | 8/2013 | Iwato | |

FOREIGN PATENT DOCUMENTS

| | | |
|---|---|---|
| CN | 102037409 A | 4/2011 |
| JP | 5-282938 A | 10/1993 |
| JP | 6-102547 A | 4/1994 |
| JP | 11258796 A | 9/1999 |
| JP | 2008281975 A | 11/2008 |
| JP | 2009025707 A | 2/2009 |
| JP | 2009173623 A | 8/2009 |
| JP | 2009173625 A | 8/2009 |
| JP | 2010139996 A | 6/2010 |
| JP | 2010164958 A | 7/2010 |
| JP | 2011-153087 A | 8/2011 |
| JP | 2012-509494 A | 4/2012 |
| JP | 2013007785 A | 1/2013 |
| JP | 2013-79230 A | 5/2013 |
| KR | 10-2011-0009708 A | 1/2011 |
| WO | 2009143357 A2 | 11/2009 |
| WO | WO 2010134639 A1 * | 11/2010 |
| WO | 2011013842 A1 | 2/2011 |
| WO | 2012036090 A1 | 3/2012 |

OTHER PUBLICATIONS

Office Action dated Nov. 25, 2014 issued by the Japan Patent Office in counterpart Japanese Patent Application No. 2012-072541.
ISR (PCT/ISA/210), issued Jun. 11, 2013, in corresponding International Application No. PCT/JP2013/060138.
Written Opinion (PCT/ISA/237), issued Jun. 11, 2013, in corresponding International Application No. PCT/JP2013/060138.
Communication issued Feb. 17, 2015, by the Japanese Patent Office in related Application No. 2012-072541.
Ouyangm et al; "Negative-Tone Development of Photoresists in Environmentally Friendly Friendly Silicone Fluids"; Proc. of SPIE; vol. 8325; 2012; pp. 832524-1 to 832524-6.
SPIE 2012 Advanced Lithography Technical Program (p. 32); 3 pages total; Feb. 2012.
Office Action dated May 24, 2016 in corresponding Taiwanese Application No. 102110790.
Office Action dated Apr. 14, 2016 issued by the Korean Intellectual Property Office in counterpart Korean Patent Application No. 10-2014-7026893.

* cited by examiner

*Primary Examiner* — Amanda C Walke
(74) *Attorney, Agent, or Firm* — Sughrue Mion, PLLC

(57) ABSTRACT

There is provided a pattern forming method comprising (i) a step of forming a film by using an actinic ray-sensitive or radiation-sensitive composition containing (A) a non-polymeric acid-decomposable compound having an aromatic ring and a molecular weight of 500 to 5,000 and (B) a compound capable of generating an acid upon irradiation with an actinic ray or radiation; (ii) a step of exposing the film, and (iii) a step of performing development by using an organic solvent-containing developer to form a negative pattern.

22 Claims, No Drawings of approximately from 45 to 100 nm is formed.

PATTERN FORMING METHOD, ACTINIC RAY-SENSITIVE OR RADIATION-SENSITIVE COMPOSITION USED THEREIN, RESIST FILM, MANUFACTURING METHOD OF ELECTRONIC DEVICE USING THE SAME, AND ELECTRONIC DEVICE

CROSS REFERENCE TO RELATED APPLICATION

This is a continuation of International Application No. PCT/JP2013/060138 filed on Mar. 27, 2013, and claims priority from Japanese Patent Application No. 2012-072541 filed on Mar. 27, 2012, the entire disclosures of which are incorporated therein by reference.

TECHNICAL FIELD

The present invention relates to a pattern forming method suitably used for the ultramicrolithography process such as production of VLSI or a high-capacity microchip or for other fabrication processes and capable of forming a highly defined pattern by using an electron beam (EB), an extreme-ultraviolet ray (EUV) or the like, an actinic ray-sensitive or radiation-sensitive composition for use in the pattern forming method, a resist film, a manufacturing method of an electronic device using the same, and an electronic device.

BACKGROUND ART

The resist material generally used heretofore is a polymer-based resist material capable of forming an amorphous thin film. For example, a resist thin film formed by coating a solution of a polymer-based resist material such as polyalkyl methacrylate (e.g., polymethyl methacrylate) and acid-dissociable reactive group-containing polyhydroxystyrene on a substrate is irradiated with an ultraviolet ray, a far ultraviolet ray, an electron beam, an extreme-ultraviolet ray (EUV), an X-ray or the like, whereby a line pattern having a line width of approximately from 45 to 100 nm is formed.

However, the polymer-based resist material has a large molecular weight of approximately from 10,000 to 100,000 and a broad molecular weight distribution and therefore, in the lithography using a polymer-based resist material, roughness is generated on the fine pattern surface, making it difficult to control the pattern dimension and leading to reduction in the yield. Thus, the conventional lithography using a polymer-based resist material as the main component has a limit in refinement. In order to produce a finer pattern, various low-molecular-weight resist materials which can be used as the main component are disclosed (see, for example, JP-A-2009-173625 (the term "JP-A" as used herein means an "unexamined published Japanese patent application"), JP-A-2009-173623, JP-A-11-258796 and Adv. Mater., 20, 3355 (2008)).

For example, JP-A-2009-173625 and JP-A-2009-173623 have reported a low-molecular-weight resist material composed of a calixarene derivative. In both reports, a pattern is formed using an alkali developer, that is, a positive pattern is formed in JP-A-2009-173625 and a negative pattern is formed in JP-A-2009-173623.

Also, JP-A-11-258796 has reported a low-molecular-weight resist material composed of a fullerene derivative, and it is indicated that a negative pattern is formed by irradiating the exposed area with an electron beam to cause chemical crosslinking and performing development using an organic solvent-containing developer.

Furthermore, Adv. Mater., 20, 3355 (2008) has reported a case of forming a positive pattern through EUV exposure and alkali development by using a low-molecular-weight resist material composed of a polynuclear phenol derivative.

These low-molecular-weight resist materials are expected to realize high resolution and excellent roughness characteristics thanks to their low molecular weight (small molecular size), but sufficient performances are not obtained so far. Among others, in the formation of an ultrafine pattern, it has been difficult to satisfy the resolution, line edge roughness (LER) and good dry etching resistance at the same time.

On the other hand, in recent years, a pattern forming method using a resist composition containing an acid-decomposable polymer material and a compound capable of generating an acid upon irradiation with an actinic ray or radiation and using an organic solvent-containing developer is also being developed (see, for example, JP-A-2008-281975, JP-A-2010-139996, JP-A-2010-164958 and JP-A-2009-25707).

For example, in JP-A-2008-281975, JP-A-2010-139996, JP-A-2010-164958 and JP-A-2009-25707, a pattern forming method including a step of subjecting a resist composition containing a polymer material having a relatively high content of a repeating unit containing a group capable of decomposing by the action of an acid to produce a polar group, to development using an organic solvent-containing developer is described. It is indicated that according to such a method, the roughness performance, dimensional uniformity and the like in forming an ultrafine pattern are excellent.

However, formation of an ultrafine pattern is difficult due to use of a polymer-based resist material as the main component and because a polar group is produced in the pattern area, the dry etching resistance needs to be improved.

SUMMARY OF INVENTION

An object of the present invention is to provide a pattern forming method capable of forming a pattern satisfying high resolution, small line edge roughness (LER) and good dry etching resistance all at the same time in forming a pattern having an ultrafine line part (for example, with a line width of 50 nm or less), an actinic ray-sensitive or radiation-sensitive composition for use in the pattern forming method, a resist film, a manufacturing method of an electronic device using the same, and an electronic device.

The present invention is as follows.

[1] A pattern forming method comprising:

(i) a step of forming a film by using an actinic ray-sensitive or radiation-sensitive composition containing (A) a non-polymeric acid-decomposable compound having an aromatic ring and a molecular weight of 500 to 5,000 and (B) a compound capable of generating an acid upon irradiation with an actinic ray or radiation, (ii) a step of exposing the film, and (iii) a step of performing development by using an organic solvent-containing developer to form a negative pattern.

[2] The pattern forming method as described in [1], wherein the compound (A) is a compound represented by the following formula (1):

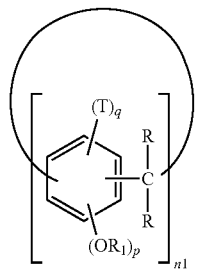

(1)

wherein each R independently represents a hydrogen atom or a substituent, and each R in the compound (A) may be the same as or different from every other R;

$OR_1$ represents a hydroxyl group or a group having a structure capable of decomposing by the action of an acid to produce a polar group, and each $OR_1$ in the compound (A) may be same as or different from every other $OR_1$, with the proviso that at least one of the plurality of $OR_1$s and the plurality of Rs is a group having a structure capable of decomposing by the action of an acid to produce a polar group;

T represents a hydrogen atom or a substituent, and when a plurality of Ts are present, each T may be the same as or different from every other T;

p represents an integer of 1 to 4;

q represents an integer represented by (4-p);

n1 represents an integer of 3 or more;

n1 ps may be the same value or different values; and n1 qs may be the same value or different values.

[3] The pattern forming method as described in [2], wherein the compound (A) is a compound represented by the following formula (2):

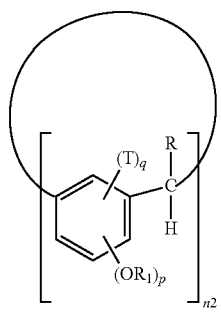

(2)

wherein $OR_1$, R, T, p and q have the same meanings as $OR_1$, R, T, p and q in formula (1), respectively, and each $OR_1$, R or T in the compound (A) may be the same as or different from every other $OR_1$, R or T, with the proviso that at least one of the plurality of $OR_1$s and the plurality of Rs is a group having a structure capable of decomposing by the action of an acid to produce a polar group;

n2 represents an integer of 3 to 8;

n2 ps may be the same value or different values; and n2 qs may be the same value or different values.

[4] The pattern forming method as described in [3], wherein the compound (A) is a compound represented by the following formula (3):

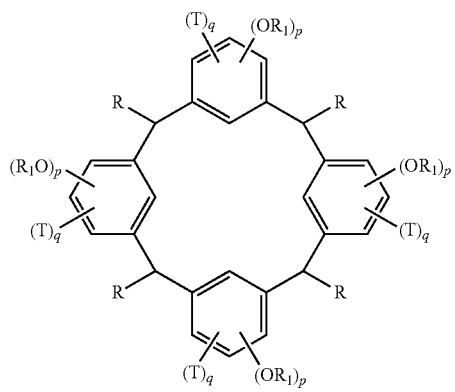

(3)

wherein $OR_1$, R, T, p and q have the same meanings as $OR_1$, R, T, p and q in formula (2), respectively, and each $OR_1$, R or T in the compound (A) may be the same as or different from every other $OR_1$, R or T, with the proviso that at least one of the plurality of $OR_1$s and the plurality of Rs is a group having a structure capable of decomposing by the action of an acid to produce a polar group;

four ps may be the same value or different values; and four qs may be the same value or different values.

[5] The pattern forming method as described in [4], wherein the compound (A) is a compound represented by the following formula (4):

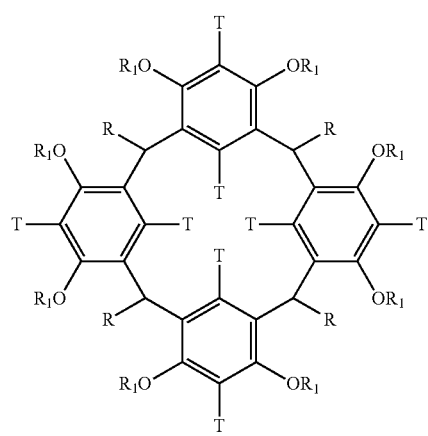

(4)

wherein $OR_1$, R and T have the same meanings as $OR_1$, R and T in formula (3), respectively, and each $OR_1$, R or T in the compound (A) may be the same as or different from every other $OR_1$, R or T, with the proviso that at least one of the plurality of $OR_1$s and the plurality of Rs is a group having a structure capable of decomposing by the action of an acid to produce a polar group.

[6] The pattern forming method as described in any one of [2] to [5], wherein R in formulae (1) to (4) is an aryl group represented by the following formula (5):

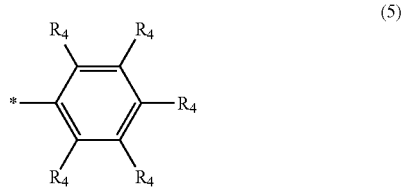

(5)

wherein each $R_4$ independently represents a hydrogen atom or a substituent, with the proviso that at least one of the plurality of $OR_1$s and the plurality of $R_4$s in the compound (A) is a group having a structure capable of decomposing by the action of an acid to produce a polar group.

[7] The pattern forming method as described in any one of [1] to [6], wherein the exposure in the step (ii) is exposure to an electron beam or an extreme-ultraviolet ray (EUV light).

[8] The pattern forming method as described in any one of [1] to [7], wherein the developer is a developer containing at least one kind of an organic solvent selected from the group consisting of a ketone-based solvent, an ester-based solvent, an alcohol-based solvent, an amide-based solvent and an ether-based solvent.

[9] The pattern forming method as described in any one of [1] to [8], further comprising:

(iv) a step of performing rinsing by using an organic solvent-containing rinsing solution.

[10] An actinic ray-sensitive or radiation-sensitive composition used for the pattern forming method described in any one of [1] to [9].

[11] A resist film formed of the actinic ray-sensitive or radiation-sensitive composition described in [10].

[12] A method for manufacturing an electronic device, comprising the pattern forming method described in any one of [1] to [9].

[13] An electronic device manufactured by the manufacturing method of an electronic device described in [12].

According to the present invention, a pattern forming method capable of forming a pattern satisfying high resolution, small line edge roughness (LER) and good dry etching resistance all at the same time in forming a pattern having an ultrafine line part (for example, with a line width of 50 nm or less), an actinic ray-sensitive or radiation-sensitive composition for use in the pattern forming method, a resist film, a manufacturing method of an electronic device using the same, and an electronic device can be provided.

DESCRIPTION OF EMBODIMENTS

The mode for carrying out the present invention is described below.

In the description of the present invention, when a group (atomic group) is denoted without specifying whether substituted or unsubstituted, the group encompasses both a group having no substituent and a group having a substituent. For example, "an alkyl group" encompasses not only an alkyl group having no substituent (unsubstituted alkyl group) but also an alkyl group having a substituent (substituted alkyl group).

In the description of the present invention, the term "actinic ray" or "radiation" indicates, for example, a bright line spectrum of mercury lamp, a far ultraviolet ray typified by excimer laser, an extreme-ultraviolet ray (EUV light), an X-ray or an electron beam (EB). Also, in the present invention, the "light" means an actinic ray or radiation.

In addition, unless otherwise indicated, the "exposure" as used in the description of the present invention encompasses not only exposure to a mercury lamp, a far ultraviolet ray typified by excimer laser, an extreme-ultraviolet ray, an X-ray, EUV light or the like but also lithography with a particle beam such as electron beam and ion beam.

The pattern forming method of the present invention is a pattern forming method comprising:

(i) a step of forming a film by using an actinic ray-sensitive or radiation-sensitive composition containing (A) a non-polymeric acid-decomposable compound having an aromatic ring and a molecular weight of 500 to 5,000 and (B) a compound capable of generating an acid upon irradiation with an actinic ray or radiation, (ii) a step of exposing the film, and (iii) a step of performing development by using an organic solvent-containing developer to form a negative pattern.

According to the pattern forming method of the present invention, a pattern forming method capable of forming a pattern satisfying high resolution, small line edge roughness (LER) and good dry etching resistance all at the same time in forming a pattern having an ultrafine line part (for example, with a line width of 50 nm or less), an actinic ray-sensitive or radiation-sensitive composition for use in the pattern forming method, a resist film, a manufacturing method of an electronic device using the same, and an electronic device can be provided. The reason therefor is not clearly known but is presumed as follows.

In the case where a pattern is formed using a general polymer-based resist material, because of the large molecular weight of the resist material, unevenness is readily produced on the side wall or the like of the line part and this is considered to lead to reduction in the resolution or line edge roughness (LER) performance. The present inventors have found that such reduction in performances is significantly noticeable when the pattern intended to obtain is a pattern having an ultrafine line part (for example, with a line width of 50 nm or less).

On the other hand, in the pattern forming method of the present invention, a non-polymeric acid-decomposable compound having a molecular weight of 500 to 5,000, that is, a low-molecular-weight resist material, is used as the resist material. As a result, unevenness on the side wall or the like of the line part is less likely to be produced, and this is considered to contribute to enhancement of the resolution and line edge roughness (LER) performance.

Also, in the case of forming a pattern having an ultrafine line part, a stronger capillary force is liable to be generated in the fine space gap formed at the development and when the developer is discharged from the space gap, the capillary force is imposed on the side wall of the pattern having a fine line width. In this connection, in the case of forming a positive pattern by using an alkali developer, the affinity of the pattern containing a resin as the main component for the alkali developer tends to be low and therefore, the capillary force imposed on the side wall of the pattern is liable to become large and cause pattern collapse.

On the other hand, in the case of forming a negative pattern by using an organic solvent-containing developer (organic developer) as in the present invention, the affinity of the pattern containing a resin as the main component for the organic developer tends to be high and therefore, the capillary force imposed on the side wall of the pattern is small to hardly allow for generation of pattern collapse. This small capillary force is considered to also contribute to enhancement of the resolution and in turn, enhancement of the line edge roughness (LER) performance.

In addition, the resist material for use in the present invention has an aromatic ring and at the same time, the molecular weight thereof is a small molecular weight as described above. Accordingly, it is considered that the carbon density in the resist material is sufficiently high and this can contribute to enhancement of the pattern strength, as a result, good dry etching resistance is achieved.

In the pattern forming method of the present invention, the developer is preferably a developer containing at least one kind of an organic solvent selected from the group consisting of a ketone-based solvent, an ester-based solvent, an alcohol-based solvent, an amide-based solvent and an ether-based solvent.

The pattern forming method of the present invention preferably further comprises (iv) a step of performing rinsing by using an organic solvent-containing rinsing solution.

The rinsing solution is preferably a rinsing solution containing at least one kind of an organic solvent selected from the group consisting of a hydrocarbon-based solvent, a ketone-based solvent, an ester-based solvent, an alcohol-based solvent, an amide-based solvent and an ether-based solvent.

The pattern forming method of the present invention preferably comprises (v) a heating step after the exposure step (ii).

The pattern forming method of the present invention may further comprise (vi) a step of performing development by using an alkali developer.

In the pattern forming method of the present invention, the exposure step (ii) may be performed a plurality of times.

In the pattern forming method of the present invention, the heating step (v) may be performed a plurality of times.

The resist film of the present invention is a film formed of the above-described actinic ray-sensitive or radiation-sensitive composition, and this film is formed, for example, by coating the actinic ray-sensitive or radiation-sensitive composition on a base material.

The actinic ray-sensitive or radiation-sensitive composition which can be used in the present invention is described below.

The present invention also relates to the actinic ray-sensitive or radiation-sensitive composition described below.

The actinic ray-sensitive or radiation-sensitive composition according to the present invention is used for negative development (development where the solubility for developer is decreased upon exposure, as a result, the exposed area remains as a pattern and the unexposed area is removed). That is, the actinic ray-sensitive or radiation-sensitive composition according to the present invention can be an actinic ray-sensitive or radiation-sensitive composition for organic solvent development, which is used for development using an organic solvent-containing developer. The term "for organic solvent development" as used herein means usage where the composition is subjected to at least a step of performing development by using an organic solvent-containing developer.

The actinic ray-sensitive or radiation-sensitive composition of the present invention is typically a resist composition and is preferably a negative resist composition (that is, a resist composition for organic solvent development), because particularly high effects can be obtained. The composition according to the present invention is typically a chemical amplification resist composition.

[1] (A) Non-Polymeric Acid-Decomposable Compound Having an Aromatic Ring and a Molecular Weight of 500 to 5,000

The actinic ray-sensitive or radiation-sensitive composition according to the present invention contains a non-polymeric acid-decomposable compound having an aromatic ring and a molecular weight of 500 to 5,000 (hereinafter, sometimes simply referred to as "compound (A)").

Here, the "non-polymeric" indicates that the compound is different from a polymer compound having a repeating unit formed by polymerizing a monomer.

That is, the non-polymeric compound for use in the present invention is a compound having a fixed molecular weight in the molecular weight range of 500 to 5,000 (a compound having substantially no molecular weight distribution), which is not a so-called polymer or oligomer obtained by cleaving an unsaturated bond of an unsaturated bond-containing compound (monomer) to cause chain growth of a bond while using an initiator.

For example, a cyclic compound having a fixed molecular weight formed by a condensation reaction falls under the "non-polymeric" compound, but an oligomer having a number average molecular weight of 500 to 5,000 does not fall under the "non-polymeric" compound.

The molecular weight of the compound (A) is not particularly limited as long as it is from 500 to 5,000, but the molecular weight is preferably from 600 to 4,000, more preferably from 700 to 3,000.

In the present invention, the compound (A) has an aromatic ring. The aromatic ring is preferably an aromatic ring having a carbon number of 6 to 20, and examples thereof include a monocyclic aromatic ring such as benzene ring, and a condensed polycyclic aromatic ring such as naphthalene ring and anthracene ring. The aromatic ring is preferably a monocyclic aromatic ring, more preferably a benzene ring.

The compound (A) preferably has from 2 to 10 aromatic rings, more preferably from 2 to 6 aromatic rings, still more preferably from 3 to 5 aromatic rings.

Furthermore, the compound (A) is an acid-decomposable compound and is typically a compound having a structure capable of decomposing by the action of an acid to produce a polar group. Details of the structure capable of decomposing by the action of an acid to produce a polar group are described later.

The compound (A) is not particularly limited but is preferably, for example, a compound represented by the following formula (1), a fullerene derivative or a polynuclear phenol derivative, more preferably a compound represented by the following formula (1):

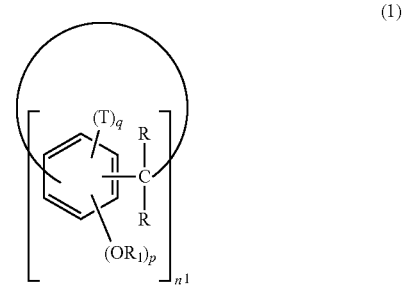

In formula (1), each R independently represents a hydrogen atom or a substituent, and each R in the compound (A) may be the same as or different from every other R.

OR$_1$ represents a hydroxyl group or a group having a structure capable of decomposing by the action of an acid to produce a polar group, and each OR$_1$ in the compound (A) may be same as or different from every other OR$_1$. However, at least one of the plurality of OR$_1$s and the plurality of Rs is a group having a structure capable of decomposing by the action of an acid to produce a polar group.

T represents a hydrogen atom or a substituent, and when a plurality of Ts are present, each T may be the same as or different from every other T.

p represents an integer of 1 to 4.

q represents an integer represented by (4-p).

n1 represents an integer of 3 or more.

n1 ps may be the same value or different values.

n1 qs may be the same value or different values.

In the case where OR$_1$ represents a hydroxyl group, R$_1$ represents a hydrogen atom.

In the case where OR$_1$ represents a group having a structure capable of decomposing by the action of an acid to produce a polar group (hereinafter, sometimes referred to as "acid-decomposable structure"), the acid-decomposable structure preferably has a structure where a polar group is protected by a group capable of leaving by the action of an acid.

The polar group is not particularly limited as long as it is a group capable of being sparingly solubilized or insolubilized in an organic solvent-containing developer, but examples thereof include a phenolic hydroxyl group, an acidic group (a group capable of dissociating in an aqueous 2.38 mass % tetramethylammonium hydroxide solution which has been conventionally used as the developer for a resist) such as carboxyl group, fluorinated alcohol group (preferably hexafluoroisopropanol group), sulfonic acid group, sulfonamide group, sulfonylimide group, (alkylsulfonyl)(alkylcarbonyl)methylene group, (alkylsulfonyl)(alkylcarbonyl)imide group, bis(alkylcarbonyl)methylene group, bis(alkylcarbonyl)imide group, bis(alkylsulfonyl)methylene group, bis(alkylsulfonyl)imide group, tris(alkylcarbonyl)methylene group and tris(alkylsulfonyl)methylene group, and an alcoholic hydroxyl group.

The alcoholic hydroxyl group is a hydroxyl group bonded to a hydrocarbon group and indicates a hydroxyl group except for a hydroxyl group directly bonded on an aromatic ring (phenolic hydroxyl group), and an aliphatic alcohol substituted with an electron-withdrawing group such as fluorine atom at the α-position (for example, a fluorinated alcohol group (e.g., hexafluoroisopropanol)) is excluded from the hydroxyl group. The alcoholic hydroxyl group is preferably a hydroxyl group having a pKa of 12 to 20.

Preferred polar groups include a carboxyl group, a fluorinated alcohol group (preferably hexafluoroisopropanol group), and a sulfonic acid group.

R$_1$ can be appropriately selected from those proposed for a hydroxystyrene-based resin, a (meth)acrylic resin and the like used in a chemical amplification resist composition for KrF or ArF, and examples thereof include a substituted methyl group, a 1-substituted ethyl group, a 1-substituted-n-propyl group, a 1-branched alkyl group, a silyl group, an acyl group, a 1-substituted alkoxymethyl group, a cyclic ether group, an alkoxycarbonyl group, and an alkoxycarbonylalkyl group.

Here, R$_1$ includes:

(a) a group capable of leaving from the oxygen atom in "OR$_1$" by the action of an acid to convert OR$_1$ into OH (that is, a phenolic hydroxyl group as the polar group) (hereinafter, sometimes referred to as "group (a)"), and (b) a group having a structure capable of producing a polar group without allowing an atom in R$_1$, which is bonded to the oxygen atom of "OR$_1$", to leave from the oxygen atom of "OR$_1$" by the action of an acid (hereinafter, sometimes referred to as "group (b)").

R$_1$ as the group (a) is a group capable of leaving by the action of an acid and is preferably a substituted methyl group, a 1-substituted ethyl group, a 1-substituted-n-propyl group, a 1-branched alkyl group, a silyl group, an acyl group, a 1-substituted alkoxymethyl group, a cyclic ether group or an alkoxycarbonyl group.

R$_1$ as the group (b) is preferably an alkoxycarbonylalkyl group. In this case, the alkoxycarbonylalkyl group as R$_1$ generates a carboxyl group as the polar group by the action of an acid.

Incidentally, R$_1$ is preferably free from a crosslinking functional group (more specifically, a crosslinking functional group capable of crosslinking with another compound (A) by the action of an acid).

The substituted methyl group is preferably a substituted methyl group having a carbon number of 2 to 20, more preferably a substituted methyl group having a carbon number of 4 to 18, still more preferably a substituted methyl group having a carbon number of 6 to 16. Examples thereof include a methoxymethyl group, a methylthiomethyl group, an ethoxymethyl group, an n-propoxymethyl group, an isopropoxymethyl group, an n-butoxymethyl group, a tert-butoxymethyl group, a 2-methylpropoxymethyl group, an ethylthiomethyl group, a methoxyethoxymethyl group, a phenylmethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, and groups represented by the following structure group (9).

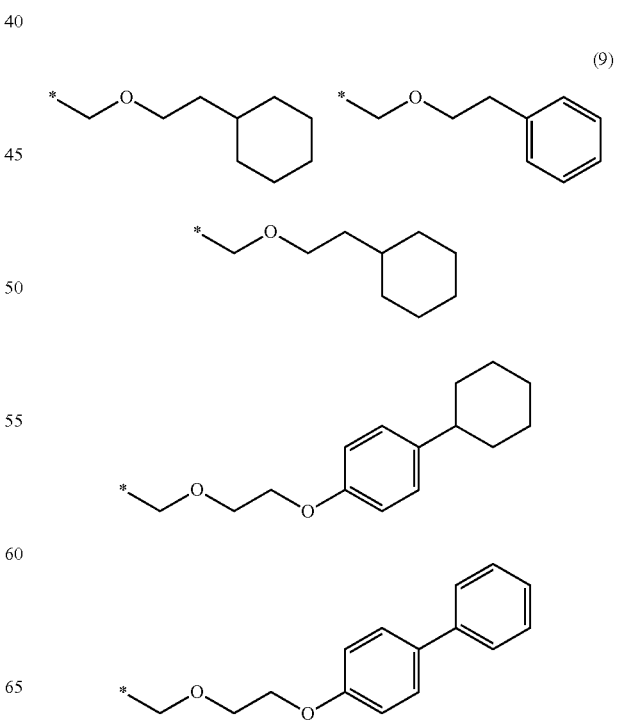

(9)

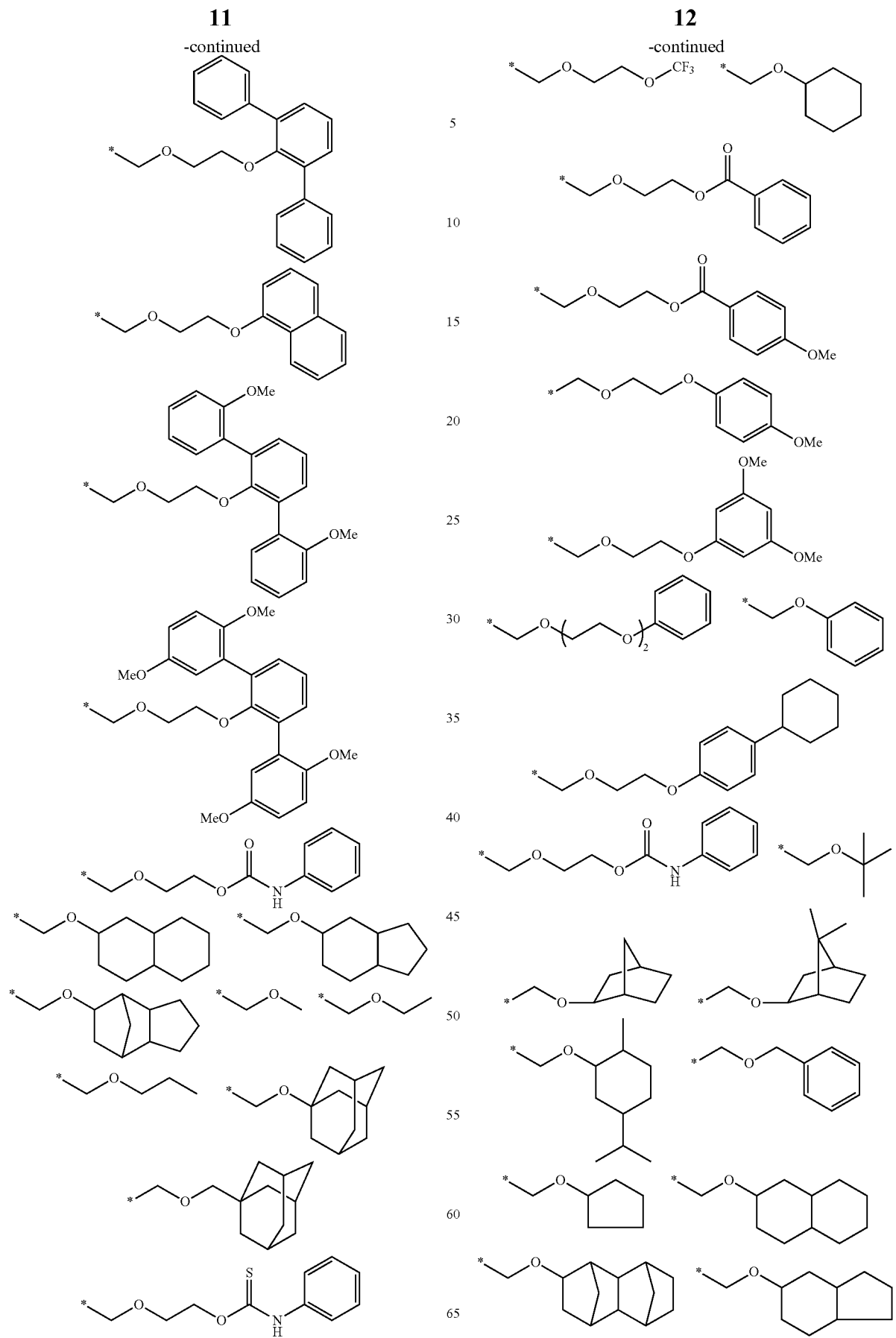

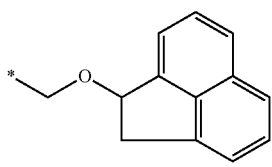
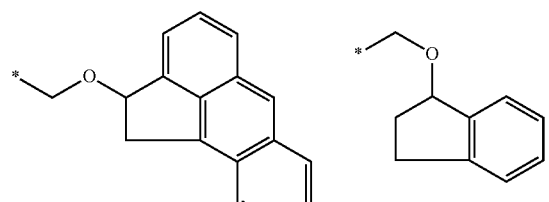
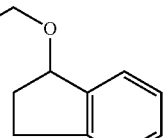
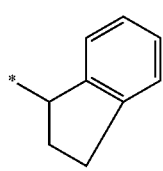

The 1-substituted ethyl group is preferably a 1-substituted ethyl group having a carbon number of 3 to 20, more preferably a 1-substituted ethyl group having a carbon number of 5 to 18, still more preferably a substituted ethyl group having a carbon number of 7 to 16. Examples thereof include a 1-methoxyethyl group, a 1-methylthioethyl group, a 1,1-dimethoxyethyl group, a 1-ethoxyethyl group, a 1-ethylthioethyl group, a 1,1-diethoxyethyl group, an n-propoxyethyl group, an iso-propoxyethyl group, an n-butoxyethyl group, a tert-butoxyethyl group, a 2-methylpropoxyethyl group, a 1-phenoxyethyl group, a 1-phenylthioethyl group, a 1,1-diphenoxyethyl group, a 1-cyclopentyloxyethyl group, a 1-cyclohexyloxyethyl group, a 1-phenylethyl group, a 1,1-diphenylethyl group, and groups represented by the following structure group (10).

(10)

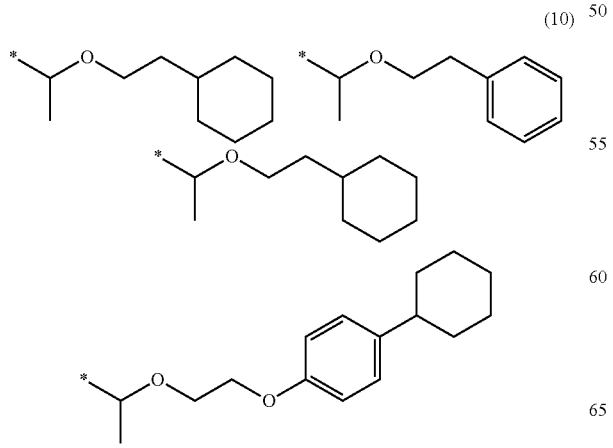

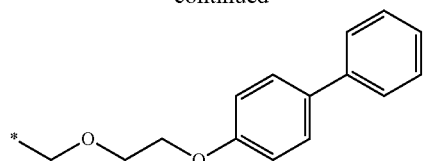
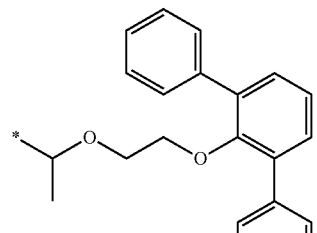
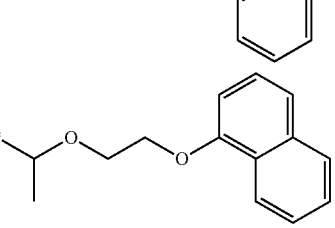
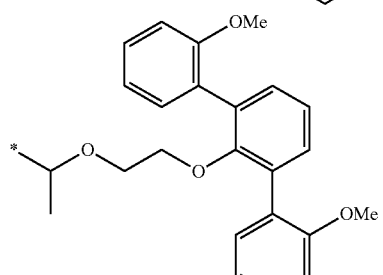
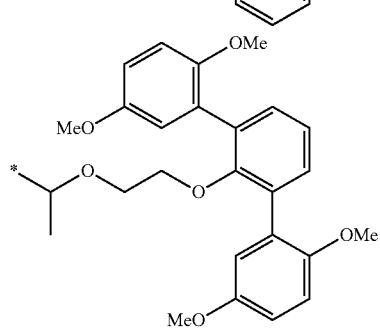
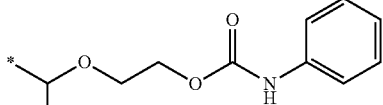
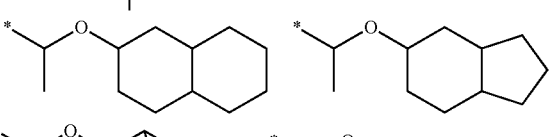
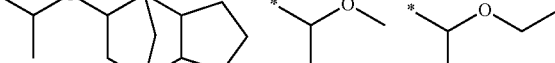
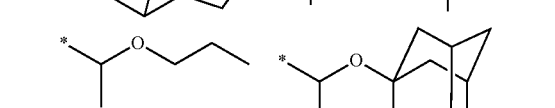

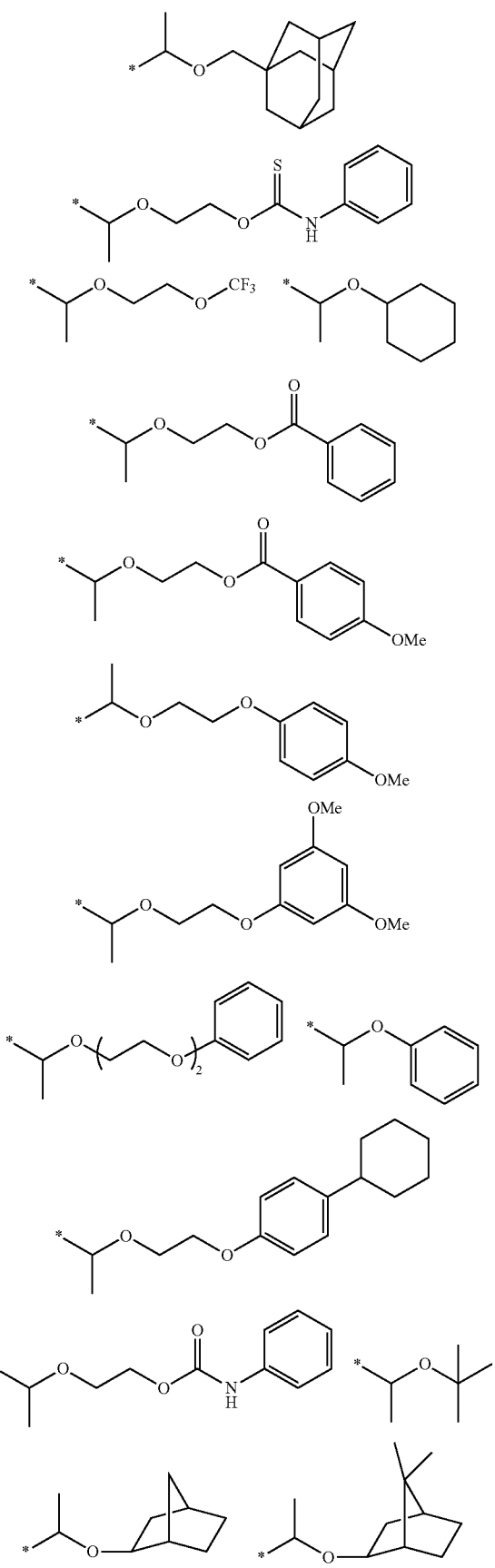
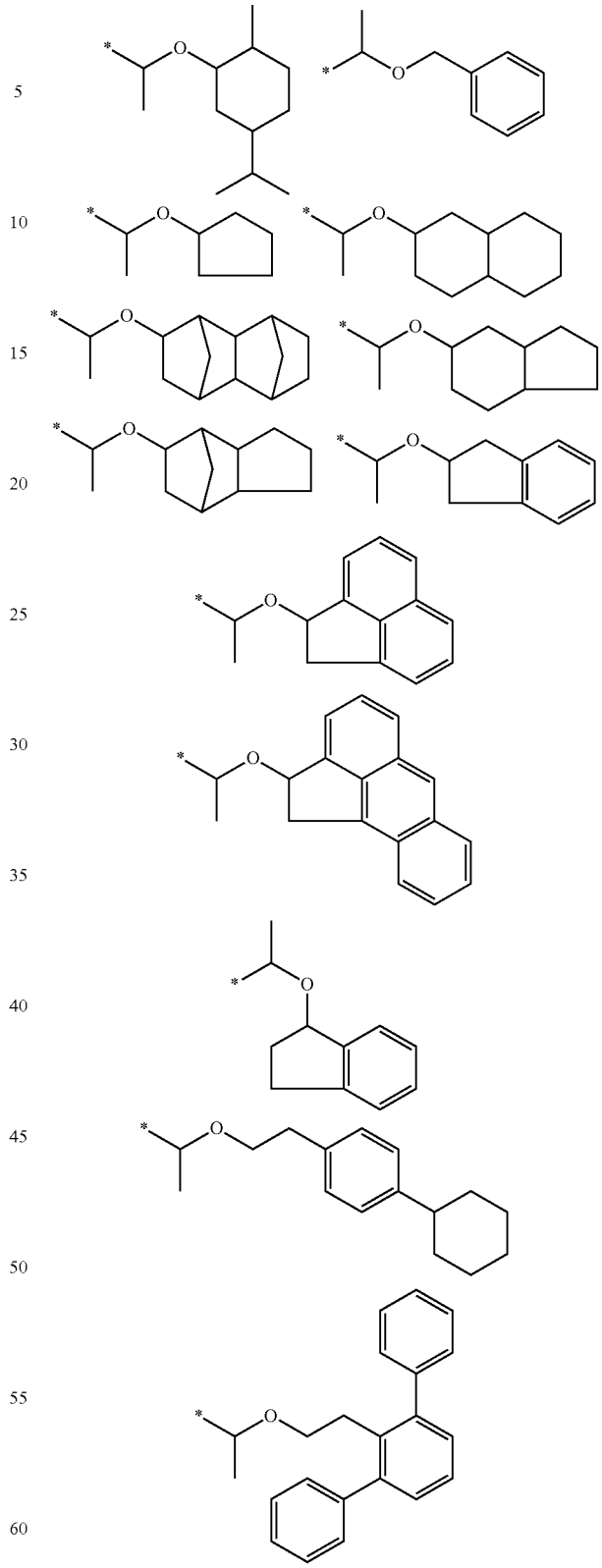
The 1-substituted-n-propyl group is preferably a 1-substituted-n-propyl group having a carbon number of 4 to 20, more preferably a 1-substituted-n-propyl group having a carbon number of 6 to 18, still more preferably a 1-substituted-n- propyl group having a carbon number of 8 to 16. Examples thereof include a 1-methoxy-n-propyl group and a 1-ethoxy-n-propyl group.

The 1-branched alkyl group is preferably a 1-branched alkyl group having a carbon number of 3 to 20, more preferably a 1-branched alkyl group having a carbon number of 5 to 18, still more preferably a branched alkyl group having a carbon number of 7 to 16. Examples thereof include an isopropyl group, a sec-butyl group, a tert-butyl group, a 1,1-dimethylpropyl group, a 1-methylbutyl group, a 1,1-dimethylbutyl group, a 2-methyladamantyl group, and a 2-ethyladamantyl group.

The silyl group is preferably a silyl group having a carbon number of 1 to 20, more preferably a silyl group having a carbon number of 3 to 18, still more preferably a silyl group having a carbon number of 5 to 16. Examples thereof include a trimethylsilyl group, an ethyldimethylsilyl group, a methyldiethylsilyl group, a triethylsilyl group, a tert-butyldimethylsilyl group, a tert-butyldiethylsilyl group, a tert-butyldiphenylsilyl group, a tri-tert-butylsilyl group, and a triphenylsilyl group.

The acyl group is preferably an acyl group having a carbon number of 2 to 20, more preferably an acyl group having a carbon number of 4 to 18, still more preferably an acyl group having a carbon number of 6 to 16. Examples thereof include an acetyl group, a phenoxyacetyl group, a propionyl group, a butyryl group, a heptanoyl group, a hexanoyl group, a valeryl group, a pivaloyl group, an isovaleryl group, a lauroyl group, an adamantylcarbonyl group, a benzoyl group, and a naphthoyl group.

The 1-substituted alkoxymethyl group is preferably a 1-substituted alkoxymethyl group having a carbon number of 2 to 20, more preferably a 1-substituted alkoxymethyl group having a carbon number of 4 to 18, still more preferably a 1-substituted alkoxymethyl group having a carbon number of 6 to 16.

Examples thereof include a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, and a 1-adamantylmethoxymethyl group.

The cyclic ether group is preferably a cyclic ether group having a carbon number of 2 to 20, more preferably a cyclic ether group having a carbon number of 4 to 18, still more preferably a cyclic ether group having a carbon number of 6 to 16. Examples thereof include a tetrahydropyranyl group, a tetrahydrofuranyl group, a tetrahydrothiopyranyl group, a tetrahydrothiofuranyl group, a 4-methoxytetrahydropyranyl group, and a 4-methoxytetrahydrothiopyranyl group.

The alkoxycarbonyl group is preferably an alkoxycarbonyl group having a carbon number of 2 to 20, more preferably an alkoxycarbonyl group having a carbon number of 4 to 18, still more preferably an alkoxycarbonyl group having a carbon number of 6 to 16. Examples thereof include a methoxycarbonyl group, an ethoxycarbonyl group, an n-propoxycarbonyl group, an isopropoxycarbonyl group, an n-butoxycarbonyl group, a tert-butoxycarbonyl group, a tert-amyloxycarbonyl group, and groups represented by the following structure group (11) where n=0.

The alkoxycarbonylalkyl group is preferably an alkoxycarbonylalkyl group having a carbon number of 3 to 20, more preferably an alkoxycarbonylalkyl group having a carbon number of 4 to 18, still more preferably an alkoxycarbonylalkyl group having a carbon number of 6 to 16. Examples thereof include a methoxycarbonylmethyl group, an ethoxycarbonylmethyl group, an n-propoxycarbonylmethyl group, an isopropoxycarbonylmethyl group, an n-butoxycarbonyl-methyl group, and groups represented by the following structure group (11) where n=1 to 4.

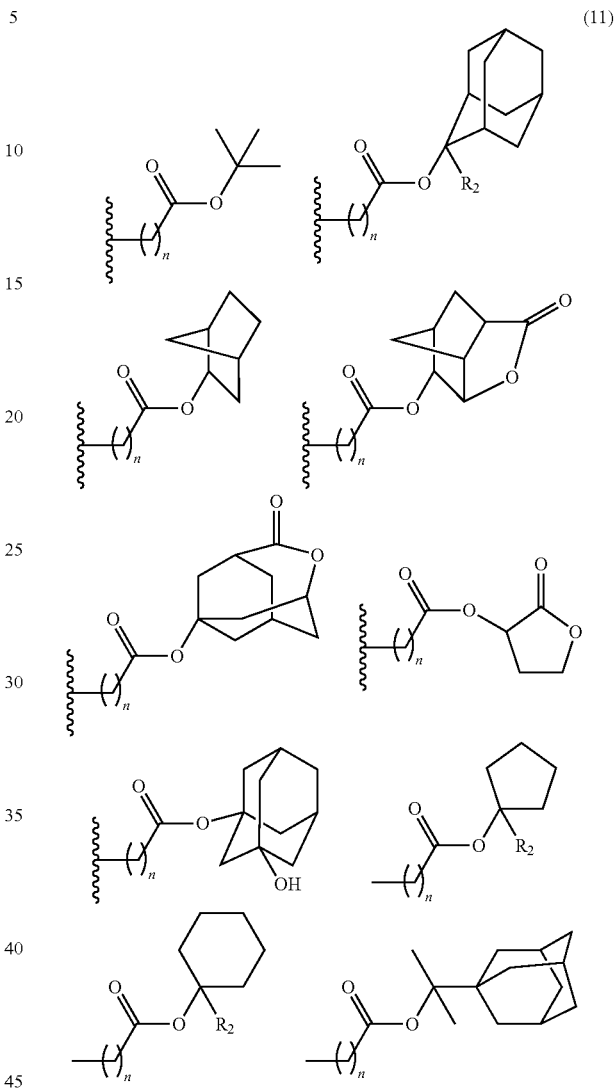

In the structure group (11), $R_2$ is a hydrogen atom or a linear or branched alkyl group having a carbon number of 1 to 4, and n is an integer of 0 to 4.

Each of the groups as $R_1$ may further have a substituent, and the substituent is not particularly limited, but examples thereof are the same as those described later for the substituent represented by T.

$R_1$ is preferably a substituted methyl group, a 1-substituted ethyl group, a 1-substituted alkoxymethyl group, a cyclic ether group, an alkoxycarbonyl group or an alkoxycarbonylalkyl group, and in view of high sensitivity, more preferably a substituted methyl group, a 1-substituted ethyl group, an alkoxycarbonyl group or an alkoxycarbonylalkyl group, still more preferably a group having a structure selected from a cycloalkane having a carbon number of 3 to 12 and an aromatic ring having a carbon number of 6 to 14. The cycloalkane having a carbon number of 3 to 12 may be monocyclic or polycyclic but is preferably polycyclic.

T represents a hydrogen atom or a substituent. The substituent as T includes an alkyl group, a cycloalkyl group, an aryl group, an aralkyl group, an acyl group, an alkoxyl group, a cyano group, a nitro group, a hydroxyl group, a heterocyclic group, a halogen atom, a carboxyl group, and an alkylsilyl group.

T is preferably a hydrogen atom, an alkyl group, a cycloalkyl group, an aralkyl group or a halogen atom, more preferably a hydrogen atom or an aralkyl group, still more preferably a hydrogen atom.

The alkyl group represented by T is preferably an alkyl group having a carbon number of 1 to 20, more preferably an alkyl group having a carbon number of 1 to 10, still more preferably an alkyl group having a carbon number of 1 to 6.

The cycloalkyl group represented by T is preferably a cycloalkyl group having a carbon number of 3 to 20, more preferably a cycloalkyl group having a carbon number of 5 to 15, still more preferably a cycloalkyl group having a carbon number of 5 to 10.

The aryl group represented by T is preferably an aryl group having a carbon number of 6 to 20, more preferably an aryl group having a carbon number of 6 to 15, still more preferably an aryl group having a carbon number of 6 to 10.

The aralkyl group represented by T is preferably an aralkyl group having a carbon number of 7 to 20, more preferably an aralkyl group having a carbon number of 7 to 15, still more preferably an aralkyl group having a carbon number of 7 to 10. Here, the aralkyl group represented by T can function also as the later-described acid-dissociable functional group.

The acyl group represented by T is preferably an acyl group having a carbon number of 2 to 20 and may be an alkylcarbonyl group or an arylcarbonyl group. Examples of the alkylcarbonyl group include an acetyl group, a propanoyl group, a butanoyl group, a hexanoyl group, a cyclohexanoyl group, an adamantanecarbonyl group, a trifluoromethylcarbonyl group, and a pentanoyl group. Examples of the arylcarbonyl group include a benzoyl group, a toluoyl group, a 1-naphthoyl group, a 2-naphthoyl group, a 4-methylsulfanylbenzoyl group, a 4-phenylsulfanylbenzoyl group, a 4-dimethylaminobenzoyl group, a 4-diethylaminobenzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethylbenzoyl group, a 3-cyanobenzoyl group, a 3-nitrobenzoyl group, a 4-fluorobenzoyl group, a 4-cyanobenzoyl group, and a 4-methoxybenzoyl group.

The alkoxyl group represented by T is preferably an alkoxyl group having a carbon number of 1 to 20, more preferably an alkoxyl group having a carbon number of 1 to 10, still more preferably an alkoxyl group having a carbon number of 1 to 6.

The heterocyclic group represented by T is preferably a heterocyclic group having a carbon number of 2 to 20, more preferably a heterocyclic group having a carbon number of 2 to 10, still more preferably a heterocyclic group having a carbon number of 2 to 6. Examples of the heterocyclic group represented by T include a pyranyl group, a thiophenyl group, an imidazolyl group, a furanyl group, and chromanyl group, with a pyranyl group, a thiophenyl group and a furanyl group being preferred.

The alkylsilyl group represented by T is preferably an alkylsilyl group having a carbon number of 1 to 20, more preferably an alkylsilyl group having a carbon number of 1 to 10, still more preferably an alkylsilyl group having a carbon number of 1 to 6.

Each of the groups as T may further have a substituent, and the substituent is not particularly limited, but examples thereof are the same as those described above for the substituent represented by T.

Examples of the substituent represented by R include an alkyl group, a cycloalkyl group, an aryl group, an aralkyl group, an acyl group, an alkoxyl group, a cyano group, a nitro group, a hydroxyl group, a heterocyclic group, a carboxyl group, an alkylsilyl group, and a group having a structure capable of decomposing by the action of an acid to produce a polar group.

Specific examples of the alkyl group, cycloalkyl group, aryl group, aralkyl group, acyl group, alkoxyl group, heterocyclic group an alkylsilyl group represented by R are the same as specific examples of respective groups in T.

The acid-decomposable structure in the "group having a structure capable of decomposing by the action of an acid to produce a polar group (hereinafter, sometimes referred to as "acid-decomposable structure")" represented by R preferably has a structure where a polar group is protected by a group capable of leaving by the action of an acid, and examples of the polar group are the same as the groups described in $OR_1$.

Also, specific examples of the "group capable of leaving by the action of an acid" in the acid-decomposable group are the same as specific examples of $R_1$ as the group (a) described in $OR_1$.

Each of the groups as R may further have a substituent, and the substituent is not particularly limited, but examples thereof are the same as those described above for the substituent represented by T.

The substituent as R is preferably an alkyl group having a carbon number of 2 to 20 or an aryl group having a carbon number of 6 to 24, more preferably an aryl group having a carbon number of 6 to 24.

Also, R is preferably an aryl group represented by the following formula (5):

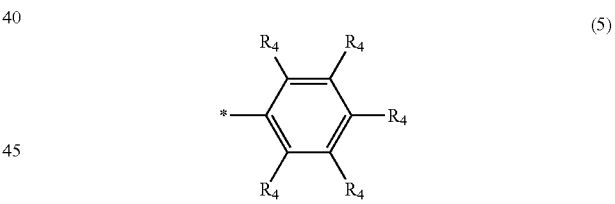

In formula (5), each $R_4$ independently represents a hydrogen atom or a substituent.

However, at least one of the plurality of $OR_1$s and the plurality of $R_4$s in the compound (A) is a group having a structure capable of decomposing by the action of an acid to produce a polar group.

In formula (5), examples of the substituent of $R_4$ include an alkyl group, a cycloalkyl group, an aryl group, an aralkyl group, an acyl group, an alkoxyl group, a cyano group, a nitro group, a hydroxyl group, a heterocyclic group, a halogen atom, a carboxyl group, an alkylsilyl group, and a group having a structure capable of decomposing by the action of an acid to produce a polar group, and specific examples of the alkyl group, cycloalkyl group, aryl group, aralkyl group, acyl group, alkoxy group, heterocyclic group and alkylsilyl group are the same as specific examples of respective groups in T.

The acid-decomposable structure in the "group having a structure capable of decomposing by the action of an acid to produce a polar group (hereinafter, sometimes referred to as "acid-decomposable structure")" represented by $R_4$ preferably has a structure where a polar group is protected by a group capable of leaving by the action of an acid, and examples of the polar group are the same as the groups described in $OR_1$.

Also, specific examples of the "group capable of leaving by the action of an acid" in the acid-decomposable group are the same as specific examples of $R_1$ as the group (a) described in $OR_1$.

Each of the groups as $R_4$ may further have a substituent, and the substituent is not particularly limited, but examples thereof are the same as those described above for the substituent represented by T.

In formula (5), $R_4$ in the para-position with respect to the bond connected to the carbon atom in formula (1) is preferably a substituent, and it is more preferred that $R_4$ in the para-position is a substituent and at the same time, both $R_4$ in the ortho-position and $R_4$ in the meta-position are a hydrogen atom.

The substituent as $R_4$ in the para-position is preferably an alkyl group, a cycloalkyl group, an aryl group, or a group having a structure capable of decomposing by the action of an acid to produce a polar group.

In formula (1), it is preferred that out of two Rs in each of n1 repeating units, one is a hydrogen atom and the other is a substituent, and preferred examples of the substituent are the same as those described above.

As described above, at least one of the plurality of $OR_1$s and the plurality of Rs (in the case where R is an aryl group represented by formula (5), the plurality of $R_4$s) in the compound (A) is a group having a structure capable of decomposing by the action of an acid to produce a polar group.

The structure capable of decomposing by the action of an acid to produce a polar group (hereinafter, sometimes referred to as "acid-decomposable structure") preferably has a structure where a polar group is protected by a group capable of leaving by the action of an acid, and examples of the polar group are the same as the groups described in $OR_1$.

Also, specific examples of the "group capable of leaving by the action of an acid" in the acid-decomposable group are the same as specific examples of $R_1$ as the group (a) described in $OR_1$.

Examples of the "group having an acid-decomposable structure" of R and $R_4$ include a group where each of the groups as R and $R_4$ is substituted with a structure capable of decomposing by the action of an acid to produce a polar group, and the structure (group) capable of decomposing by the action of an acid to produce a polar group.

The ratio of the "group having an acid-decomposable structure" to the total of all $OR_1$s and $R_4$s in formula (1) is, in terms of the molar ratio, preferably from 1 to 50%, more preferably from 5 to 40%, still more preferably from 10 to 40%.

p is an integer of 1 to 4, preferably an integer of 1 to 3, more preferably 2 or 3, still more preferably 2.

n1 is an integer of 3 or more, preferably an integer of 3 to 8, more preferably 4, 6 or 8, still more preferably 4 or 6, yet still more preferably 4.

The compound (A) is preferably a compound represented by the following formula (2):

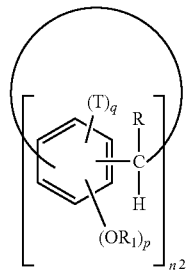

In formula (2), $OR_1$, R, T, p and q have the same meanings as $OR_1$, R, T, p and q in formula (1), respectively, and each $OR_1$, R or T in the compound (A) may be the same as or different from every other $OR_1$, R or T. However, at least one of the plurality of $OR_1$s and the plurality of Rs is a group having a structure capable of decomposing by the action of an acid to produce a polar group.

n2 represents an integer of 3 to 8.

n2 ps may be the same value or different values.

n2 qs may be the same value or different values.

Specific examples and preferred examples of $R_1$, R, T, p and q are the same as those described for $R_1$, R, T, p and q in formula (1).

n2 is preferably 4, 6 or 8, more preferably 4 or 6, still more preferably 4.

The compound (A) represented by formula (2) is preferably a compound represented by the following formula (3):

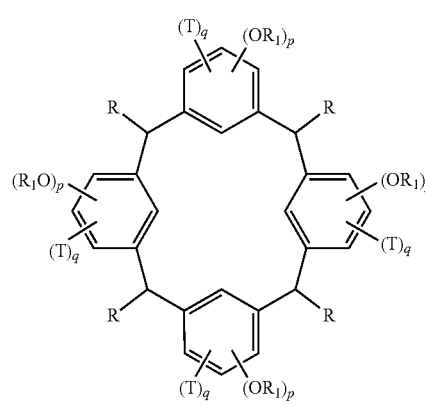

In formula (3), $OR_1$, R, T, p and q have the same meanings as $OR_1$, R, T, p and q in formula (2), respectively, and each $OR_1$, R or T in the compound (A) may be the same as or different from every other $OR_1$, R or T. However, at least one of the plurality of $OR_1$s and the plurality of Rs is a group having a structure capable of decomposing by the action of an acid to produce a polar group.

Four ps may be the same value or different values.

Four qs may be the same value or different values.

Specific examples and preferred examples of $R_1$, R, T, p and q are the same as those described for $R_1$, R, T, p and q in formula (2).

The compound represented by formula (3) is preferably a compound represented by the following formula (3'):

(3')

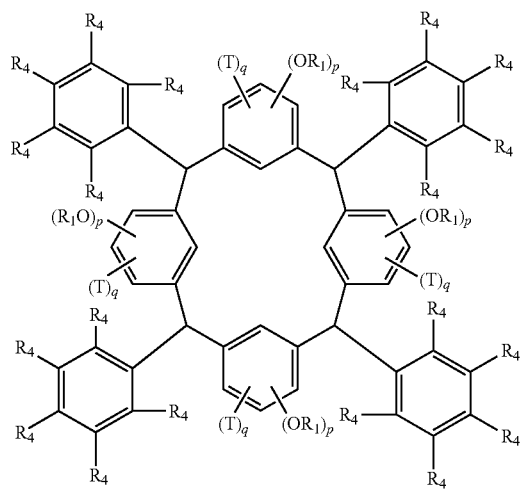

In formula (3'), $OR_1$, T, p and q have the same meanings as $OR_1$, T, p and q in formula (3), respectively.

Each $R_4$ has the same meaning as $R_4$ in formula (5).

Each $OR_1$, T or $R_4$ in the compound (A) may be the same as or different from every other $OR_1$, T or $R_4$. However, at least one of the plurality of $OR_1$s and the plurality of $R_4$s is a group having a structure capable of decomposing by the action of an acid to produce a polar group.

Four ps may be the same value or different values.

Four qs may be the same value or different values.

Specific examples and preferred examples of $R_1$, T, p and q are the same as those described for $R_1$, T, p and q in formula (3).

Specific examples and preferred examples of $R_4$ are the same as those described for $R_4$ in formula (5).

The compound represented by formula (3) is preferably a compound represented by the following formula (4):

(4)

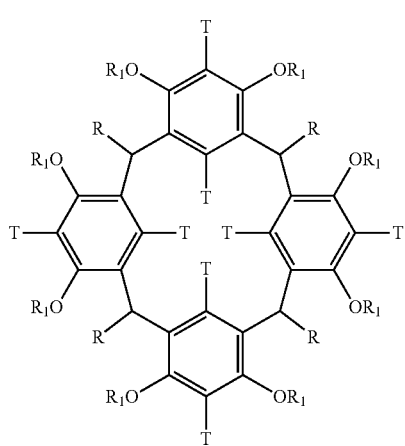

In formula (4), $OR_1$, R and T have the same meanings as $OR_1$, R and T in formula (3), respectively, and each $OR_1$, R or T in the compound (A) may be the same as or different from every other $OR_1$, R or T. However, at least one of the plurality of $OR_1$s and the plurality of Rs is a group having a structure capable of decomposing by the action of an acid to produce a polar group.

Specific examples and preferred examples of $R_1$, R and T are the same as those described for $R_1$, R and T in formula (3).

The compounds represented by formulae (1) to (5) have high heat resistance and excellent film-forming property thanks to their amorphousness, are free from sublimability and excellent, for example, in the solubility (developability) for an organic solvent-containing developer and dry etching resistance, and are suitably used as a resist material, particularly, as a main component (base material) of a resist material.

Specific examples of the compound (A) are illustrated below, but the present invention is not limited thereto.

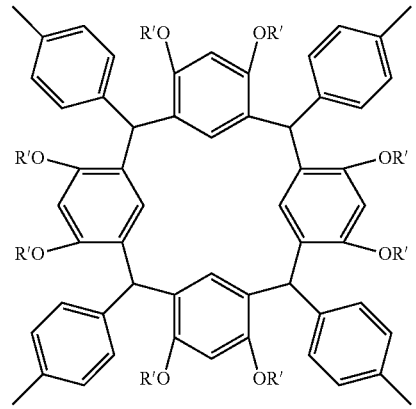

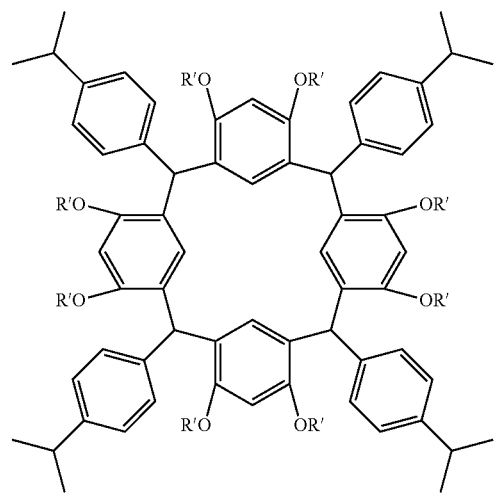

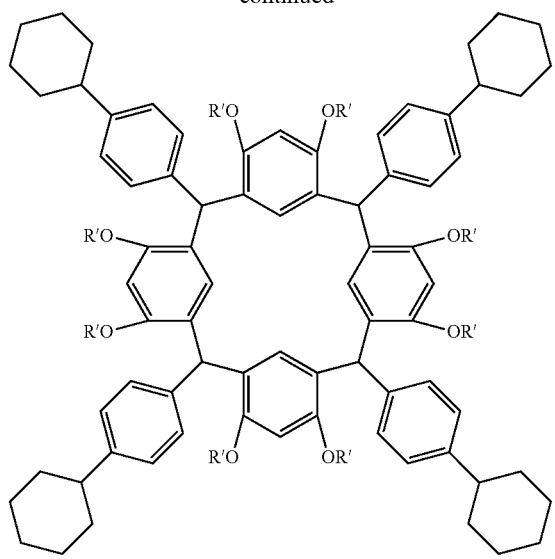
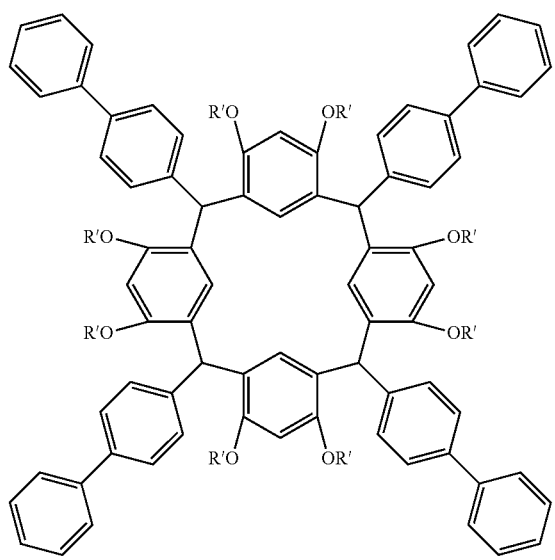
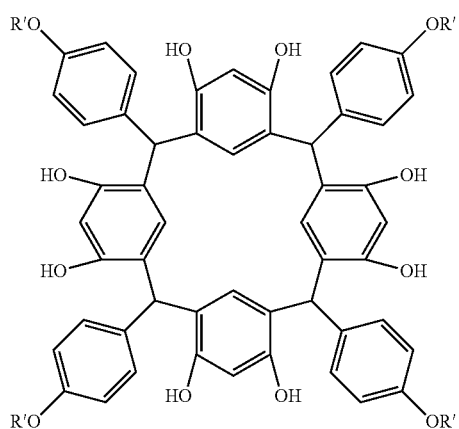
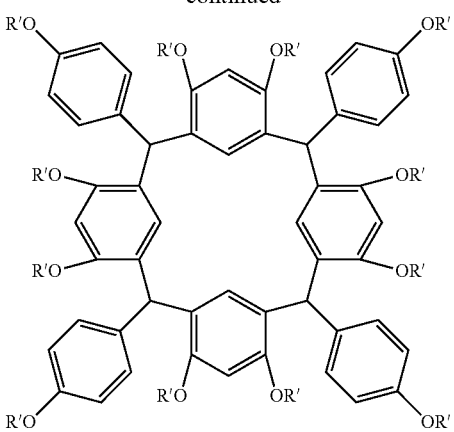
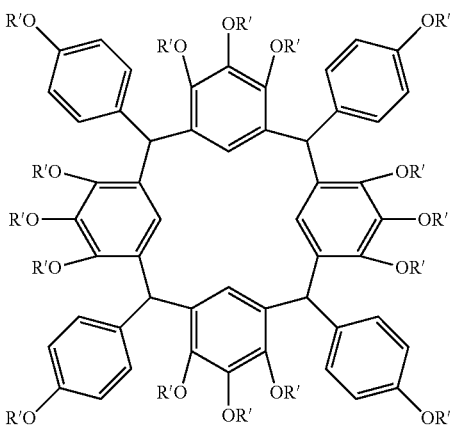
In these specific examples, each R' independently represents a hydrogen atom or the following structure (* represents a bond connected to the oxygen atom in —OR'). However, at least one of the plurality of R's present in the molecule represents the following structure (n represents 1 or 2).
R' =
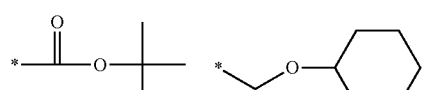
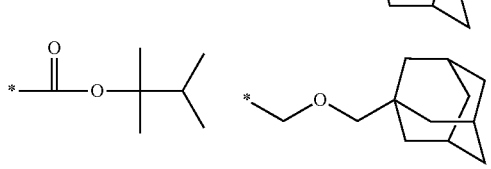

-continued

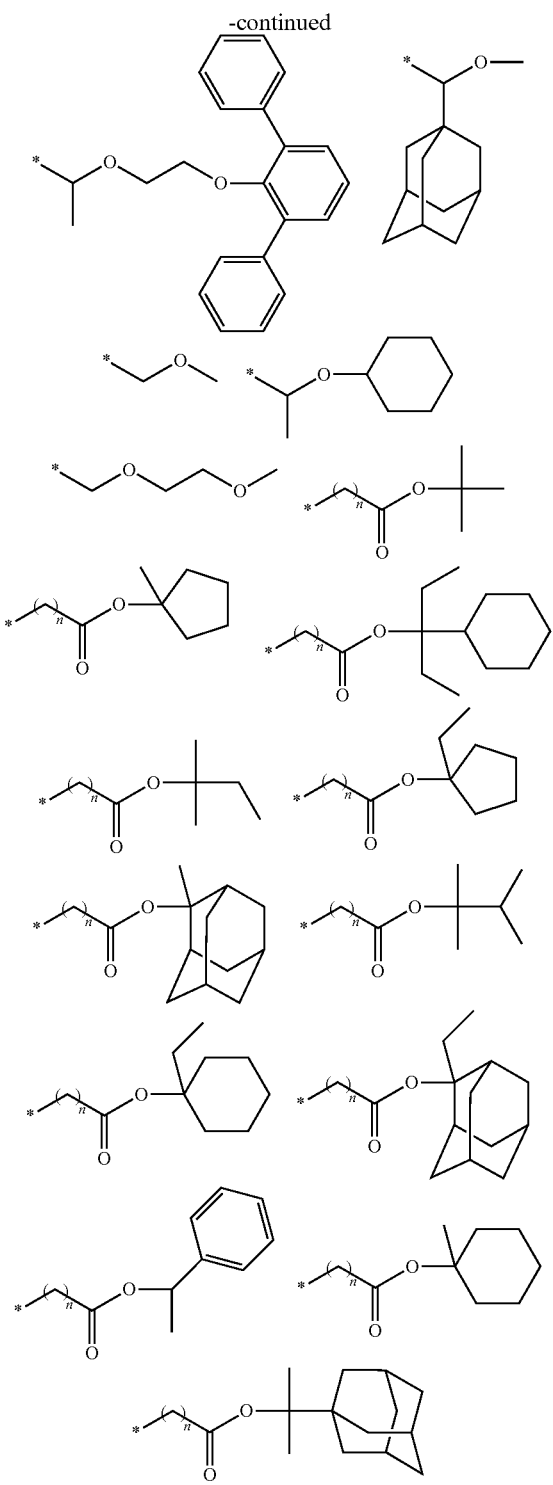

The compound (A) for use in the present invention can be produced in a high yield by a dehydrating condensation reaction starting from various aldehydes including an aromatic aldehyde produced in industry and phenols such as resorcinol and pyrogallol and using a nonmetallic catalyst such as hydrochloric acid and therefore, not only can provide the above-described effects but also is very excellent in view of production.

The compound (A) for use in the present invention may take a cis-form or a trans-form and may be either one or a mixture of these structures. In the case of using the compound as a resist component of an actinic ray-sensitive or radiation-sensitive composition, it is preferred to have only either one structure of a cis-form and a trans-form, because the compound becomes a pure compound and the uniformity of the component in the resist film is high. The method for obtaining a cyclic compound having only either one structure of a cis-form and a trans-form may be performed by a known method such as separation by column chromatography or preparative liquid chromatography and optimization of reaction solvent, reaction temperature and the like in the production.

The compound (A) for use in the present invention can be synthesized by condensation between a corresponding aldehyde compound and a phenolic compound. The acid-decomposable structure contained in the compound (A) for use in the present invention may be introduced into an aldehyde compound before condensation or may be introduced by a known method after condensation. The compound (A) can be easily synthesized, for example, by the method described in *Proc. of SPIE*, Vol. 72732Q and JP-A-2009-173625.

The compound (A) may be purified, if desired, so as to reduce the residual metal amount. Also, remaining of an acid catalyst and a promoter generally causes decrease in the storage stability of the actinic ray-sensitive or radiation-sensitive composition, or remaining of a basic catalyst generally causes decrease in the sensitivity of the actinic ray-sensitive or radiation-sensitive composition, and for the purpose of reducing the remaining catalyst, purification may be performed. The purification may be performed by a known method as long as the compound (A) is not denatured, and the method is not particularly limited but examples thereof include a method of washing the compound with water, a method of washing the compound with an acidic aqueous solution, a method of washing the compound with a basic aqueous solution, a method of treating the compound with an ion exchange resin, and a method of treating the compound with a silica gel column chromatography. The purification is preferably performed by combining two or more of these purification methods. As for the acidic aqueous solution, basic aqueous solution, ion exchange resin and silica gel column chromatography, an optimal material can be appropriately selected according to the amount and kind of the metal, acidic compound and/or basic compound to be removed, the kind of the compound (A) purified, and the like. For example, the acidic aqueous solution includes an aqueous hydrochloric acid, nitric acid or acetic acid solution having a concentration of 0.01 to 10 mol/L; the basic aqueous solution includes an aqueous ammonia solution having a concentration of 0.01 to 10 mol/L; and the ion exchange resin includes a cation exchange resin such as Amberlyst 15J-HG Dry produced by Organo Corporation. After the purification, drying may be performed. The drying can be performed by a known method, and the method is not particularly limited but examples thereof include a method of performing vacuum drying or hot-air drying under the conditions not denaturing the compound (A).

The compound (A) is preferably low in the sublimability under normal pressure at 100° C. or less, preferably at 120° C. or less, more preferably at 130° C. or less, still more preferably at 140° C. or less, yet still more preferably at 150° C. or less. The low sublimability means that in a thermogravimetric analysis, the weight loss after holding at a predetermined temperature for 10 minutes is 10%, preferably 5%, more preferably 3%, still more preferably 1%, yet still more preferably 0.1%. or less. Thanks to low sublimability, the exposure apparatus can be prevented from contamination by outgassing during exposure. Also, a good pattern profile with low LER can be provided.

The compound (A) preferably satisfies F<3.0 (F indicates: total number of atoms/(total number of carbon atoms−total number of oxygen atoms)), more preferably F<2.5. By satisfying this condition, excellent dry etching resistance is obtained.

The compound (A) has a property of dissolving in a solvent that is selected from propylene glycol monomethyl ether acetate, propylene glycol monomethyl ether, 2-heptanone, anisole, butyl acetate, ethyl propionate and ethyl lactate and exhibits a highest ability of dissolving the compound (A), in an amount of preferably 1 wt % or more, more preferably 3 wt % or more, still more preferably 5 wt % or more, yet still more preferably 10 wt % or more, at 23° C. By satisfying such conditions, use of a safety solvent in the semiconductor production process becomes possible.

The glass transition temperature of the compound (A) is preferably 100° C. or more, more preferably 120° C. or more, still more preferably 140° C. or more, yet still more preferably 150° C. or more. By virtue of having a glass transition temperature in the range above, heat resistance high enough to maintain the pattern profile during the semiconductor lithography process is obtained and a performance such as high resolution can be imparted.

The crystallization calorific value of the compound (A) as determined by a differential scanning calorimetry analysis is preferably less than 20 J/g. Also, the (crystallization temperature)−(glass transition temperature) is preferably 70° C. or more, more preferably 80° C. or more, still more preferably 100° C. or more, yet still more preferably 130° C. or more. When the crystallization calorific value is less than 20 J/g or the (crystallization temperature)−(glass transition temperature) is in the range above, an amorphous film is easily formed by spin-coating the resist composition and at the same time, the film-forming property required of the resist can be maintained over a long period of time, so that the resolution can be enhanced.

In the present invention, the crystallization calorific value, the crystallization temperature and the glass transition temperature can be measured as follows by using DSC/TA-50WS manufactured by Shimadzu Corporation and be determined by a differential scanning calorimetry analysis. About 10 mg of a sample is placed in a non-sealed aluminum-made vessel and heated to a temperature not less than the melting point at a temperature rise rate of 20° C./min in a nitrogen gas flow (50 ml/min). The sample is rapidly cooled and thereafter, again heated to a temperature not less than the melting point at a temperature rise rate of 20° C./min in a nitrogen gas flow (30 ml/min). Furthermore, the sample is rapidly cooled and thereafter, again heated to 400° C. at a temperature rise rate of 20° C./min in a nitrogen gas flow (30 ml/min). The temperature at the midpoint of a region where a discontinuous portion appears on the base line (the point where the specific heat is changed to half) is taken as the glass transition temperature (Tg), and the temperature of an exothermic peak developed thereafter is taken as the crystallization temperature. The calorific value is determined from the area of the region surrounded by the exothermic peak and the base line and taken as the crystallization calorific value.

As for the compound (A), two or more compounds may be mixed and used.

The amount added of the compound (A) for use in the present invention is preferably from 30 to 99.9 mass %, more preferably from 50 to 99.7 mass %, still more preferably from 60 to 99.5 mass %, based on the total solid content of the composition. (In this specification, mass ratio is equal to weight ratio.)

[2] (B) Compound Capable of Generating an Acid Upon Irradiation with an Actinic Ray or Radiation The actinic ray-sensitive or radiation-sensitive composition of the present invention further contains, as an essential component, (B) a compound capable of generating an acid upon irradiation with an actinic ray or radiation (hereinafter, sometimes simply referred to as "acid generator"). In the present invention, the compound (B) capable of generating an acid upon irradiation with an actinic ray or radiation may be a low molecular acid generator capable of generating an acid upon irradiation with an actinic ray or radiation (particularly, an electron beam or an extreme-ultraviolet ray), or an acid-generating polymer compound.

A preferred embodiment of the acid generator is an onium compound. Examples of the onium compound include a sulfonium salt, an iodonium salt, and a phosphonium salt.

Another preferred embodiment of the acid generator is a compound capable of generating a sulfonic acid, an imide acid or a methide acid upon irradiation with an actinic ray or radiation. Examples of the acid generator in this embodiment include a sulfonium salt, an iodonium salt, a phosphonium salt, an oxime sulfonate, and an imidosulfonate.

The acid generator for use in the present invention is not limited to a low molecular compound, and a compound where a group capable of generating an acid upon irradiation with an actinic ray or radiation is introduced into the main or side chain of a polymer compound may be also used.

The acid generator is preferably a compound capable of generating an acid upon irradiation with an electron beam or an extreme-ultraviolet ray.

In the present invention, preferred onium compounds include a sulfonium compound represented by the following formula (I) and an iodonium compound represented by formula (II):

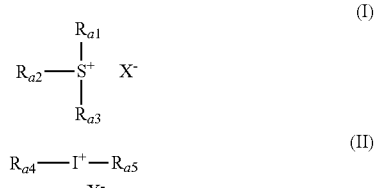

In formulae (I) and (II), each of $R_{a1}$, $R_{a2}$, $R_{a3}$, $R_{a4}$ and $R_{a5}$ independently represents an organic group.

$X^-$ represents an organic anion.

The sulfonium compound represented by formula (1) and the iodonium compound represented by formula (II) are described in more detail below.

Each of $R_{a1}$ to $R_{a3}$ in formula (I) and $R_{a4}$ and $R_{a5}$ in formula (II) independently represents an organic group, but each of at least one of $R_{a1}$ to $R_{a3}$ and at least one of $R_{a4}$ and $R_{a5}$ is preferably an aryl group. The aryl group is preferably a phenyl group or a naphthyl group, more preferably a phenyl group.

Examples of the organic anion of $X^-$ in formulae (I) and (II) include a sulfonate anion, a carboxylate anion, a bis(alkylsulfonyl)amide anion, and a tris(alkylsulfonyl)methide anion. The organic anion is preferably an organic anion represented by the following formula (III), (IV) or (V), more preferably an organic anion represented by the following formula (III):

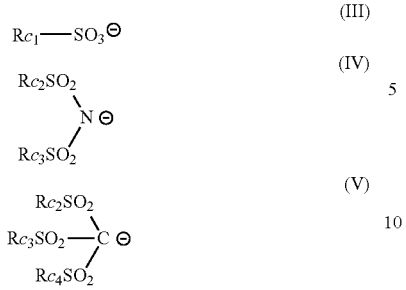

In formulae (III), (IV) and (V), each of $Rc_1$, $Rc_2$, $Rc_3$ and $Rc_4$ represents an organic group.

The organic anion of $X^-$ corresponds to a sulfonic acid, an imide acid, a methide acid or the like, which are an acid generated upon irradiation with an actinic ray or radiation such as electron beam and extreme-ultraviolet ray.

Examples of the organic group of $Rc_1$ to $Rc_4$ include an alkyl group, a cycloalkyl group, an aryl group, and a group formed by combining a plurality of these groups. Among these organic groups, an alkyl group substituted with a fluorine atom or a fluoroalkyl group at the 1-position, a cycloalkyl group substituted with a fluorine atom or a fluoroalkyl group, and a phenyl group substituted with a fluorine atom or a fluoroalkyl group are preferred. A plurality of the organic groups of $R_{c2}$ to $R_{c4}$ may combine with each other to form a ring, and the group formed by combining a plurality of these organic groups is preferably an alkylene group substituted with a fluorine atom or a fluoroalkyl group. By virtue of containing a fluorine atom or a fluoroalkyl group, the acidity of the acid generated upon irradiation with light is increased and in turn, the sensitivity is enhanced. However, a fluorine atom is preferably not contained as a substituent in the terminal group.

In the present invention, from the standpoint of improving the resolution (for example, resolving power and LER) by preventing the acid generated upon exposure from diffusing into the unexposed area, the compound (B) capable of generating an acid is preferably a compound capable of generating an acid having a size of 130 $Å^3$ or more in volume (preferably a sulfonic acid), more preferably a compound capable of generating an acid having a size of 190 $Å^3$ or more in volume (preferably a sulfonic acid), still more preferably a compound capable of generating an acid having a size of 230 $Å^3$ or more in volume (preferably a sulfonic acid), yet still more preferably a compound capable of generating an acid having a size of 270 $Å^3$ or more in volume (preferably a sulfonic acid), even yet still more preferably a compound capable of generating an acid having a size of 400 $Å^3$ or more in volume (preferably a sulfonic acid). However, in view of sensitivity and solubility in a coating solvent, the volume above is preferably 2,000 $Å^3$ or less, more preferably 1,500 $Å^3$ or less. This value is determined using "WinMOPAC" produced by Fujitsu Limited. That is, first, the chemical structure of the acid according to each example is input, and next, using this structure as the initial structure, the most stable conformation of each acid is determined by molecular force field calculation using an MM3 method. Thereafter, with respect to the most stable conformation, molecular orbital calculation using a PM3 method is performed, whereby the "accessible volume" of each acid can be computed.

Examples of the acid generator particularly preferred in the present invention are illustrated below. In some of these examples, a computed value of volume (unit: $Å^3$) is shown together. The computed value determined here is a volume value of an acid in which a proton is bonded to the anion moiety.

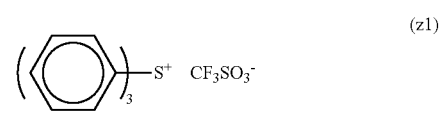

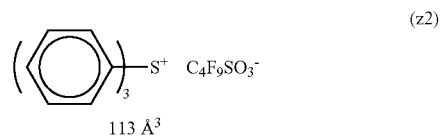

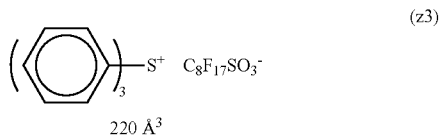

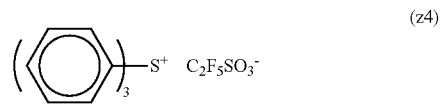

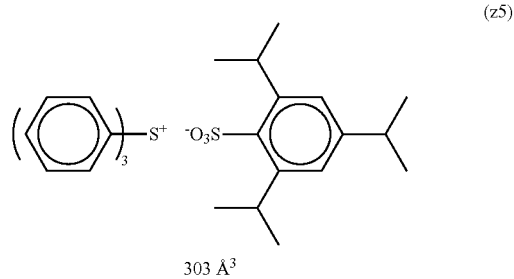

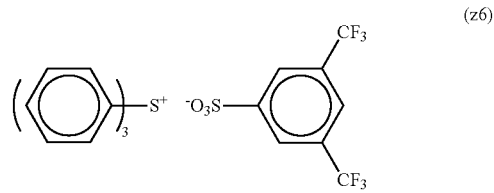

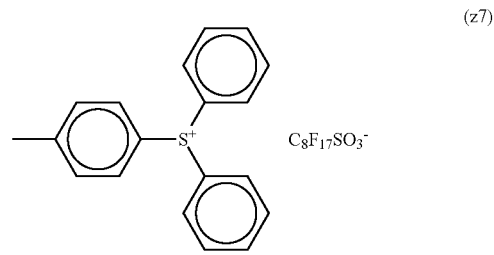

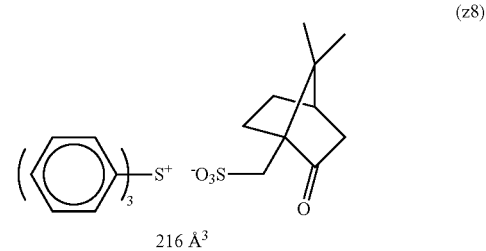

(z9)
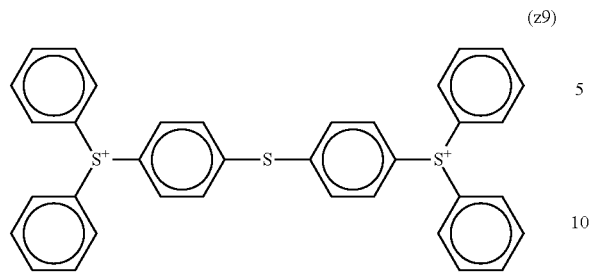
127 Å³
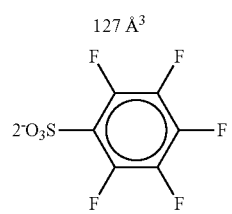
(z10)
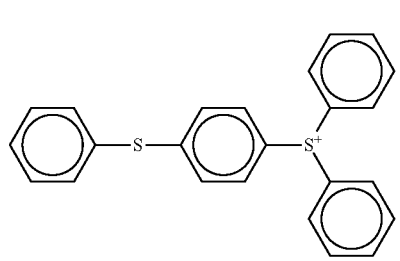
127 Å³
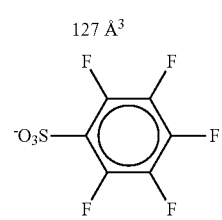
(z11)
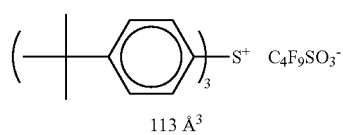
113 Å³
(z12)
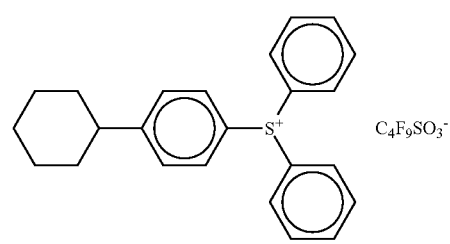
113 Å³
(z13)
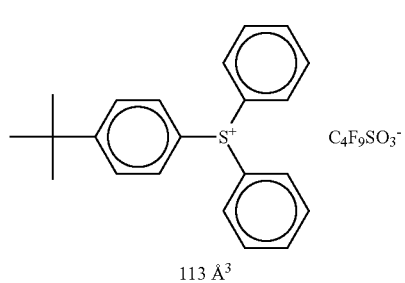
113 Å³
(z14)
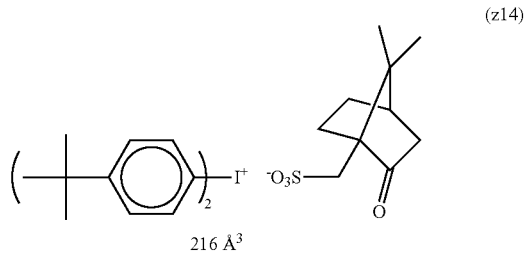
216 Å³
(z15)
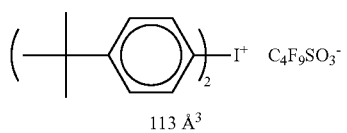
113 Å³
(z16)
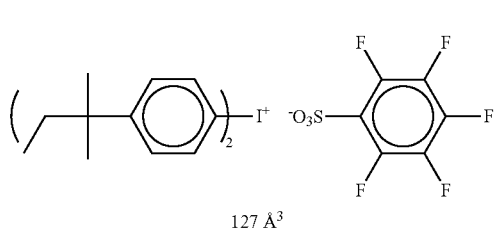
127 Å³
(z17)
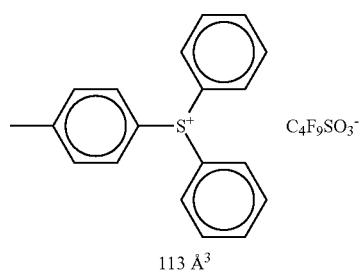
113 Å³
(z18)
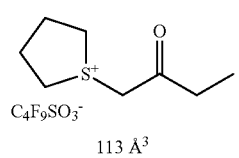
113 Å³
(z19)
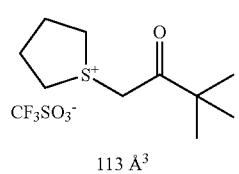
113 Å³
(z20)
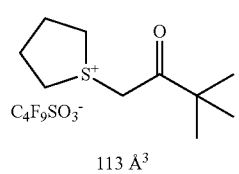
113 Å³
(z21)
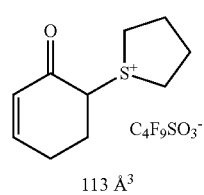
113 Å³

-continued
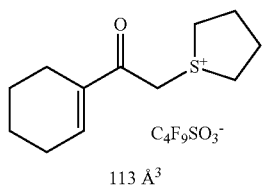
(z22)
113 Å³
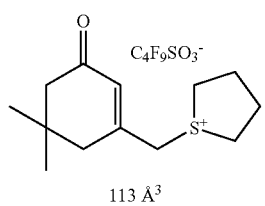
(z23)
113 Å³
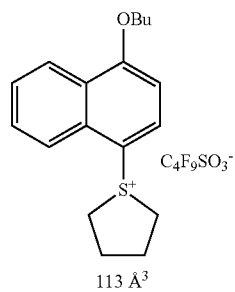
(z24)
113 Å³
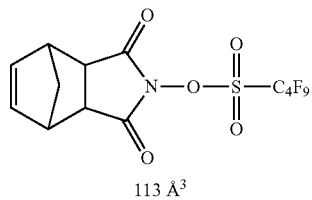
(z25)
113 Å³
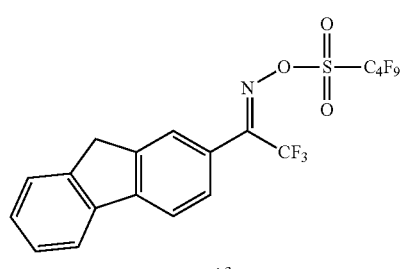
(z26)
113 Å³
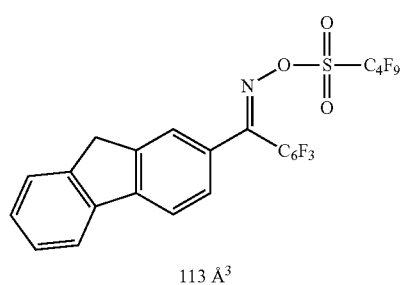
(z27)
113 Å³
-continued
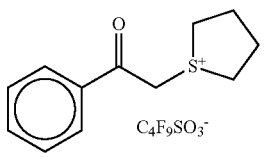
(z28)
113 Å³
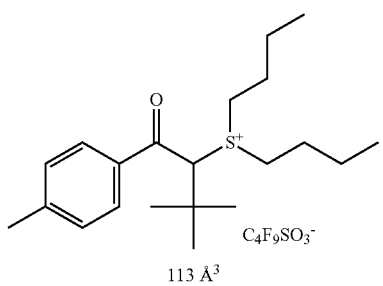
(z29)
113 Å³
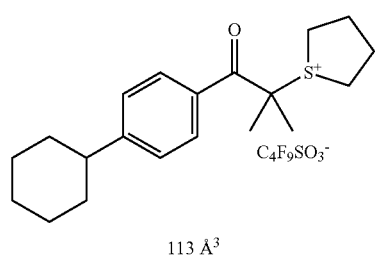
(z30)
113 Å³
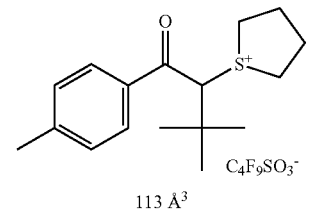
(z31)
113 Å³
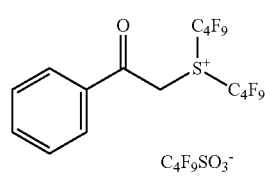
(z32)
113 Å³
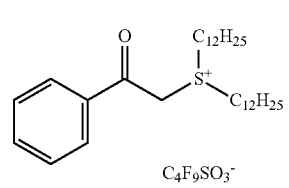
(z33)
113 Å³
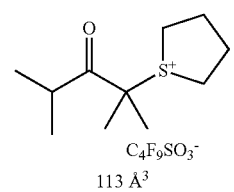
(z34)
113 Å³

-continued
(z35)
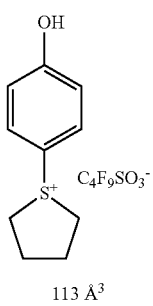
113 Å³
(z36)
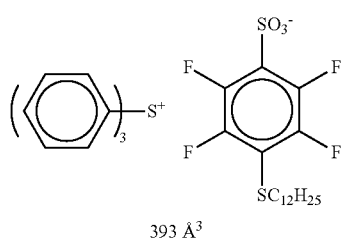
393 Å³
(z37)
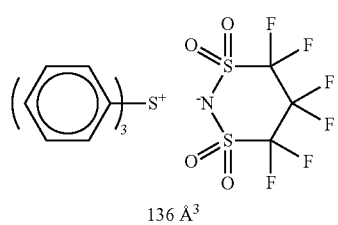
136 Å³
(z38)
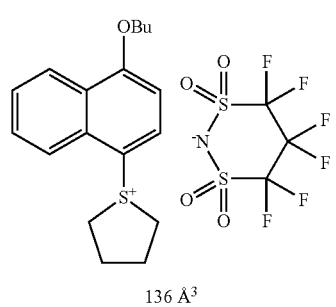
136 Å³
(z39)
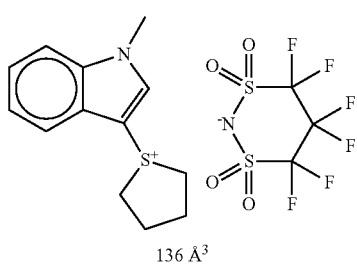
136 Å³
(z40)
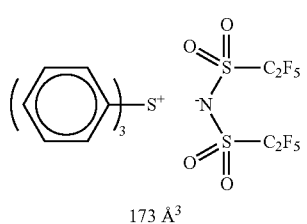
173 Å³
-continued
(z41)
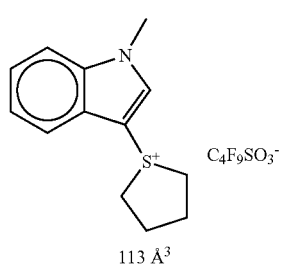
113 Å³
(z42)
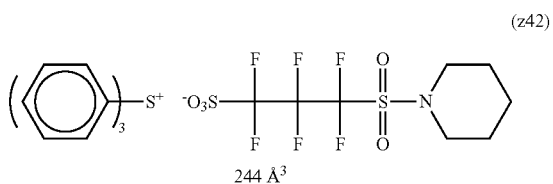
244 Å³
(z43)
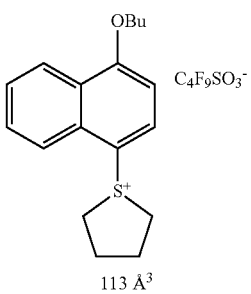
113 Å³
(z44)
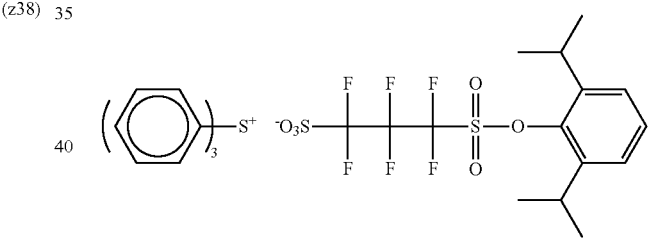
347 Å³
(z45)
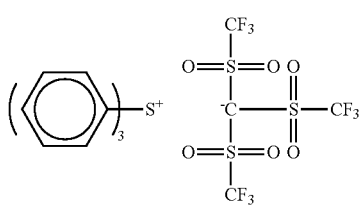
189 Å³
(z46)
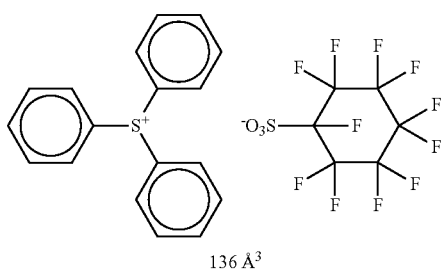
136 Å³

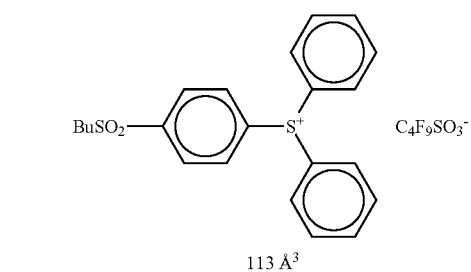
(z47)
113 Å³
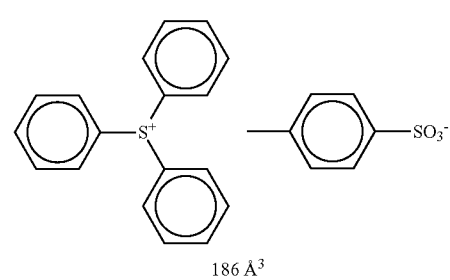
(z48)
186 Å³
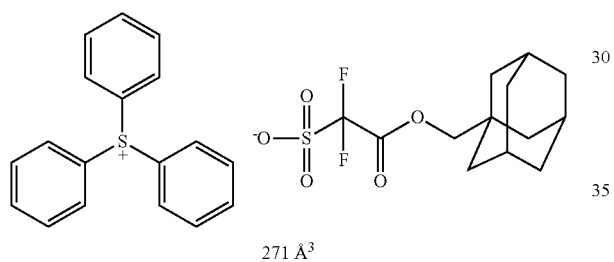
(z49)
271 Å³
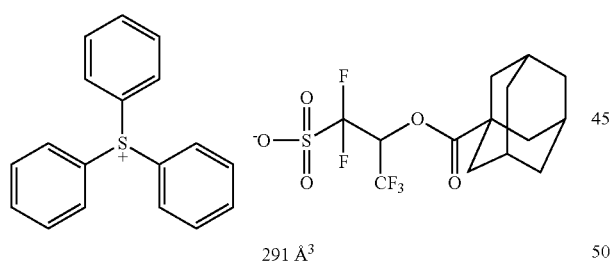
(z50)
291 Å³
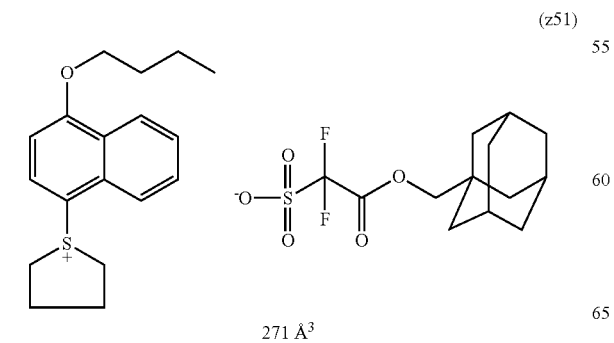
(z51)
271 Å³
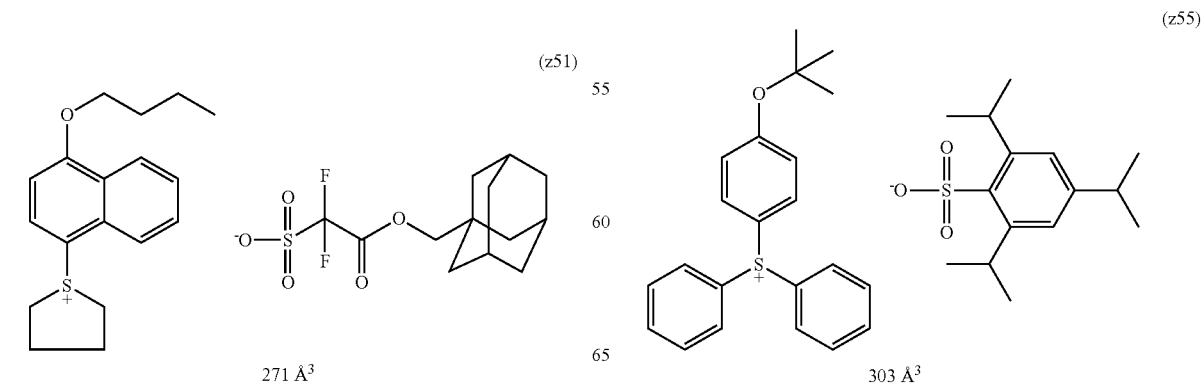
(z52) 244 Å³
(z53) 437 Å³
(z54) 303 Å³
(z55) 303 Å³

-continued
(z56)
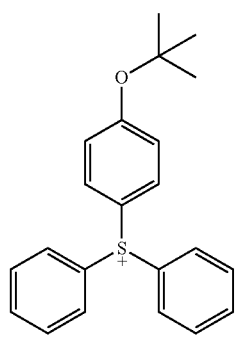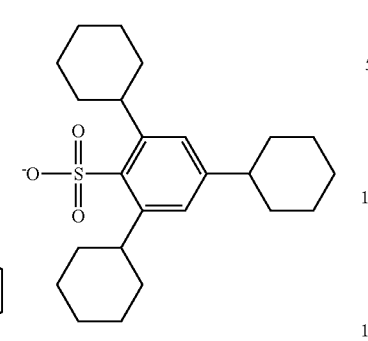
437 Å³
(z57)
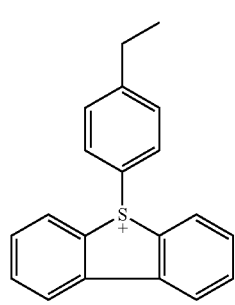
271 Å³
(z58)
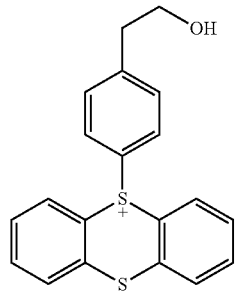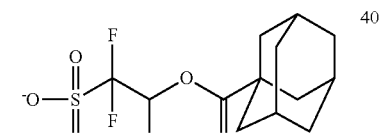
291 Å³
(z59)
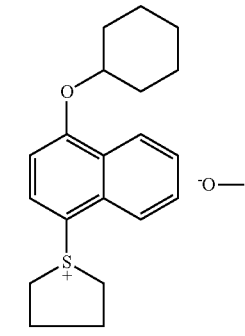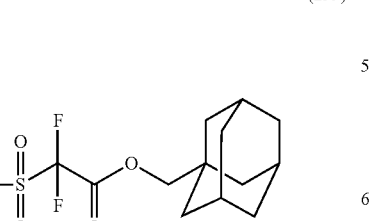
271 Å³
-continued
(z60)
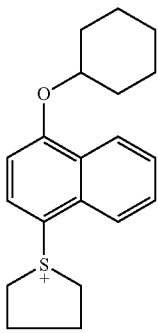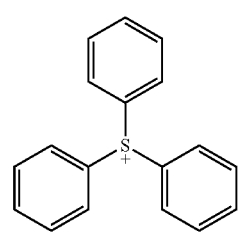
244 Å³
(z61)
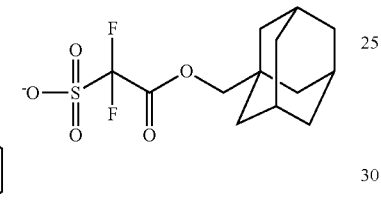
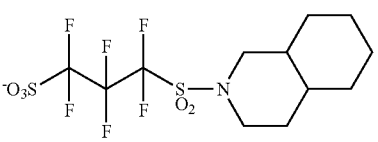
311 Å³
(z62)
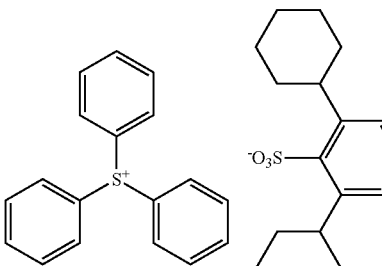
437 Å³
(z63)
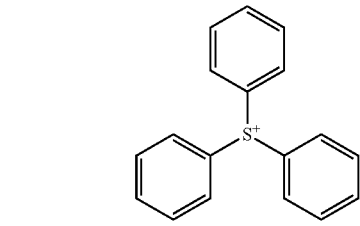

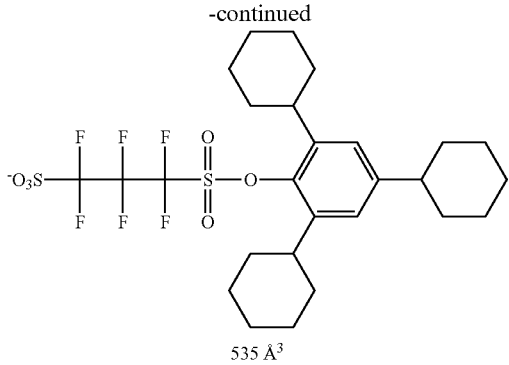

535 Å³

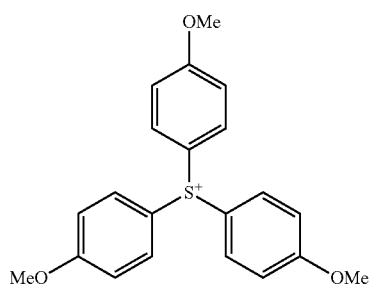

(z64)

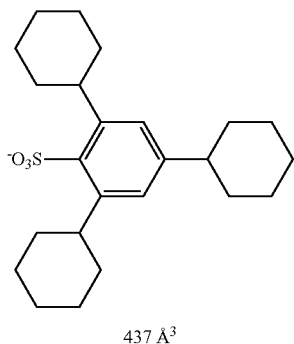

437 Å³

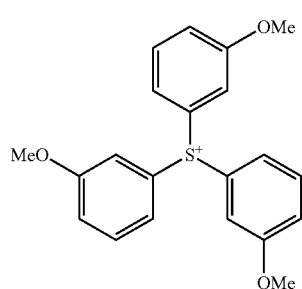

(z65)

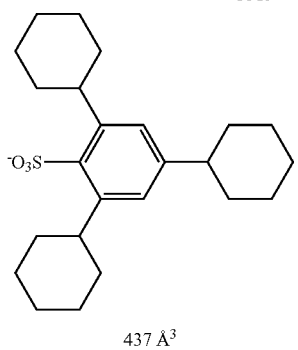

437 Å³

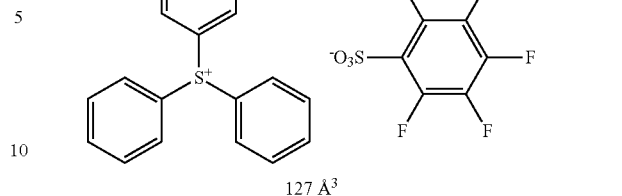

127 Å³ (z66)

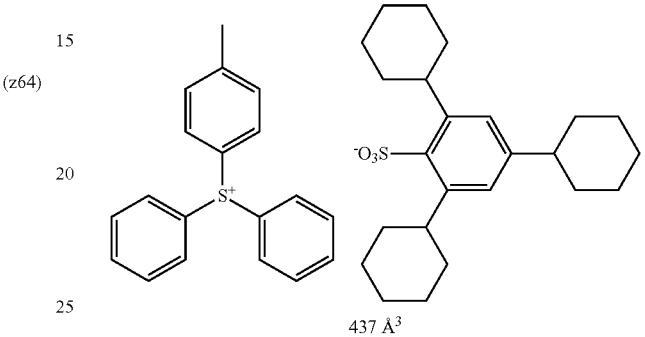

437 Å³ (z67)

The content of the acid generator in the composition is preferably from 0.1 to 25 mass %, more preferably from 0.5 to 20 mass %, still more preferably from 1 to 18 mass %, based on the total solid content of the actinic ray-sensitive or radiation-sensitive composition.

Only one acid generator may be used alone, or two or more acid generators may be used in combination.

[3] (C) Basic Compound

The actinic ray-sensitive or radiation-sensitive composition of the present invention preferably contains a basic compound as an acid scavenger, in addition to the components described above. By using a basic compound, the change of performance with aging from exposure to post-baking can be reduced. The basic compound is preferably an organic basic compound, and specific examples thereof include aliphatic amines, aromatic amines, heterocyclic amines, nitrogen-containing compounds having a carboxyl group, nitrogen-containing compounds having a sulfonyl group, nitrogen-containing compounds having a hydroxy group, nitrogen-containing compounds having a hydroxyphenyl group, alcoholic nitrogen-containing compounds, amide derivatives, and imide derivatives. An amine oxide compound (described in JP-A-2008-102383) and an ammonium salt (preferably a hydroxide or a carboxylate; more specifically, a tetraalkylammonium hydroxide typified by tetrabutylammonium hydroxide is preferred in view of LER) may be also appropriately used. Furthermore, a compound capable of increasing the basicity by the action of an acid can be also used as a kind of the basic compound.

Specific examples of the amines include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, N,N-dihexylaniline, 2,6-diisopropylaniline, 2,4,6-tri(tert-butyl)aniline, triethanolamine, N,N-dihydroxyethylaniline, tris(methoxyethoxyethyl)amine, compounds exemplified in column 3, line 60 et seq. of U.S. Pat. No.

6,040,112, 2-[2-{2-(2,2-dimethoxy-phenoxyethoxy)ethyl}-bis-(2-methoxyethyl)]-amine, and Compounds (C1-1) to (C3-3) illustrated in paragraph [0066] of U.S. Patent Application Publication No. 2007/0224539A1.

Examples of the compound having a nitrogen-containing heterocyclic structure include 2-phenylbenzimidazole, 2,4,5-triphenylimidazole, N-hydroxyethylpiperidine, bis(1,2,2,6,6-pentamethyl-4-piperidyl)sebacate, 4-dimethylaminopyridine, antipyrine, hydroxyantipyrine, 1,5-diazabicyclo[4.3.0]-non-5-ene, and 1,8-diazabicyclo[5.4.0]-undec-7-ene. The ammonium salt is preferably tetrabutylammonium hydroxide.

In addition, a photodecomposable basic compound (a compound which initially exhibits basicity due to the action of a basic nitrogen atom as a base but decomposes upon irradiation with an actinic ray or radiation to generate a zwitterionic compound having a basic nitrogen atom and an organic acid moiety and resulting from their neutralization in the molecule, is reduced in or deprived of the basicity; for example, onium salts described in Japanese Patent No. 3,577,743, JP-A-2001-215689, JP-A-2001-166476 and JPA-2008-102383), and a photobase generator (for example, compounds described in JPA-2010-243773) may be also appropriately used.

Among these basic compounds, an ammonium salt and a photodecomposable basic compound are preferred in view of pattern profile.

In the present invention, one basic compound may be used alone, or two or more basic compounds may be used in combination.

The content of the basic compound for use in the present invention is preferably from 0.01 to 10 mass %, more preferably from 0.03 to 5 mass %, still more preferably from 0.05 to 3 mass %, based on the total solid content of the actinic ray-sensitive or radiation-sensitive composition.

[4] Surfactant

In the actinic ray-sensitive or radiation-sensitive composition of the present invention, a surfactant may be further added so as to enhance the coatability. Examples of the surfactant include a nonionic surfactant such as polyoxyethylene alkyl ethers, polyoxyethylene alkylallyl ethers, polyoxyethylene-polyoxypropylene block copolymers, sorbitan fatty acid esters and polyoxyethylene sorbitan fatty acid esters, a fluorine-containing surfactant such as Florad FC430 (produced by Sumitomo 3M, Inc.), Surfynol E1004 (produced by Asahi Glass Co., Ltd.), PF656 and PF6320 produced by OMNOVA, and an organosiloxane polymer.

In the case where the actinic ray-sensitive or radiation-sensitive composition contains a surfactant, the amount of the surfactant used is preferably from 0.0001 to 2 mass %, more preferably from 0.0005 to 1 mass %, based on the total amount of the resist composition (excluding the solvent).

[5] Organic Carboxylic Acid

The chemical amplification resist composition of the present invention preferably contains an organic carboxylic acid, in addition to the components described above. Examples of the organic carboxylic acid compound include an aliphatic carboxylic acid, an alicyclic carboxylic acid, an unsaturated aliphatic carboxylic acid, an oxycarboxylic acid, an alkoxycarboxylic acid, a ketocarboxylic acid, a benzoic acid derivative, a phthalic acid, a terephthalic acid, an isophthalic acid, a 2-naphthoic acid, a 1-hydroxy-2-naphthoic acid, and a 2-hydroxy-3-naphthoic acid. At the time of performing electron beam exposure in vacuum, the organic carboxylic acid may vaporize from the resist film surface to contaminate the lithography chamber and therefore, the preferred compound is an aromatic organic carboxylic acid. Above all, for example, a benzoic acid, a 1-hydroxy-2-naphthoic acid and a 2-hydroxy-3-naphthoic acid are preferred.

The amount of the organic carboxylic acid blended is preferably from 0.01 to 10 parts by mass, more preferably from 0.01 to 5 parts by mass, still more preferably from 0.01 to 3 parts by mass, per 100 parts by mass of the compound (A).

[6] Others

The actinic ray-sensitive or radiation-sensitive composition of the present invention may further contain, if desired, a dye, a plasticizer, a photodecomposable base compound, a photobase generator and the like. Examples of such compounds include those described for respective compounds in JP-A-2002-6500.

Preferred examples of the organic solvent used for the resist composition of the present invention include ethylene glycol monoethyl ether acetate, cyclohexanone, 2-heptanone, propylene glycol monomethyl ether (PGME, another name: 1-methoxy-2-propanol), propylene glycol monomethyl ether acetate (PGMEA, another name: 1-methoxy-2-acetoxypropane), propylene glycol monomethyl ether propionate, propylene glycol monoethyl ether acetate, methyl 3-methoxypropionate, ethyl 3-ethoxypropionate, methyl β-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methylpyrrolidone, N,N-dimethylformamide, γ-butyrolactone, N,N-dimethylacetamide, propylene carbonate, and ethylene carbonate. One of these solvents is used alone, or some are used in combination.

The actinic ray-sensitive or radiation-sensitive composition is preferably prepared by dissolving the components in the solvent above to give a solid content of, in terms of solid content concentration, from 0.5 to 20 mass %, more preferably from 0.7 to 15 mass %, still more preferably from 1.0 to 10 mass %. By adjusting the solid content concentration to the range above, the later-described film thickness can be achieved.

[7] Pattern Forming Method

The pattern forming method (negative pattern forming method) of the present invention comprises at least:

(i) a step of forming a film (resist film) from an actinic ray-sensitive or radiation-sensitive composition, (ii) a step of exposing the film, and (iii) a step of performing development by using an organic solvent-containing developer.

The exposure in the step (ii) may be immersion exposure.

The pattern forming method of the present invention preferably has (iv) a heating step after the exposure step (ii).

The pattern forming method of the present invention may further have (v) a step of performing development by using an alkali developer.

In the pattern forming method of the present invention, the exposure step (ii) may be performed a plurality of times.

In the pattern forming method of the present invention, the heating step (v) may be performed a plurality of times.

The resist film is a film formed from the above-described actinic ray-sensitive or radiation-sensitive composition according to the present invention and, more specifically, is preferably formed on a substrate. In the pattern forming method of the present invention, the step of forming a film on a substrate by using an actinic ray-sensitive or radiation-sensitive composition, the step of exposing the film, and the development step can be performed by generally known methods.

In the present invention, the substrate on which the film is formed is not particularly limited, and an inorganic substrate such as silicon, SiN, $SiO_2$ and SiN, a coating-type inorganic substrate such as SOG, or a substrate generally used in the process of producing a semiconductor such as IC or producing a liquid crystal device or a circuit board such as thermal head or in the lithography of other photo-fabrication processes can be used. If desired, an organic antireflection film may be formed between the film and the substrate.

According to the actinic ray-sensitive or radiation-sensitive composition containing the compound (A), an amorphous film can be formed of solid components of the composition by using, for example, spin-coating. The dissolution rate for an organic solvent-containing developer at 23° C. of the amorphous film formed by spin-coating the actinic ray-sensitive or radiation-sensitive composition is preferably from 0.5 to 10.0 nm/sec, more preferably from 1.0 to 7.0 nm/sec, still more preferably from 1.0 to 5.0 nm/sec.

It is also preferred to include, after film formation, a pre-baking step (PB) before entering the exposure step.

Furthermore, it is also preferred to include a post-exposure baking step (PEB) after the exposure step but before the development step.

As for the heating temperature, both PB and PEB are preferably performed at 70 to 130° C., more preferably at 80 to 120° C.

The heating time is preferably from 30 to 300 seconds, more preferably from 30 to 180 seconds, still more preferably from 30 to 90 seconds.

The heating can be performed using a device attached to an ordinary exposure/developing machine or may be performed using a hot plate or the like.

Thanks to baking, the reaction in the exposed area is accelerated, and the sensitivity and pattern profile are improved.

The light source used for the exposure device in the present invention is not limited in its wavelength, but examples of the light include infrared light, visible light, ultraviolet light, far ultraviolet light, extreme-ultraviolet ray (EUV light), X-ray, and electron beam. The light is preferably far ultraviolet light having a wavelength of 250 nm or less, more preferably 220 nm or less, still more preferably from 1 to 200 nm, and specific examples thereof include KrF excimer laser (248 nm), ArF excimer laser (193 nm), $F_2$ excimer laser (157 nm), X-ray, EUV light (13 nm), and electron beam. Among these, KrF excimer laser, EUV light and electron beam are preferred, and EUV light and electron beam are more preferred.

After the amorphous film is exposed in a desired pattern to an actinic ray or radiation such as KrF excimer laser, extreme-ultraviolet ray, electron beam and X-ray and then heated, if desired, at 20 to 250° C., the dissolution rate for an organic solvent-containing developer at 23° C. of the amorphous film is not particularly limited but is preferably 0.1 nm/sec or less, more preferably 0.05 nm/sec or less, still more preferably 0.01 nm/sec or less. By satisfying the range above, the dissolution contrast between the unexposed area soluble in an organic solvent-containing developer and the exposed area insoluble in an organic solvent-containing developer is increased due to change in the solubility resulting from decomposition of the acid-decomposable structure of the compound (A) by the action of an acid, as a result, the resolution is enhanced and LER is reduced.

In the case where the pattern forming method of the present invention further includes a step of performing development by using an alkali developer, the alkali developer which can be used includes, for example, an alkaline aqueous solution of inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, or cyclic amines such as pyrrole and piperidine.

This alkaline aqueous solution may be also used after adding thereto alcohols and a surfactant each in an appropriate amount.

The alkali concentration of the alkali developer is usually from 0.1 to 20 mass %.

The pH of the alkali developer is usually from 10.0 to 15.0.

In particular, an aqueous solution of 2.38 mass % tetramethylammonium hydroxide is preferred.

As for the rinsing solution in the rinsing treatment performed after the alkali development, pure water is used, and the pure water may be used after adding thereto a surfactant in an appropriate amount.

After the development or rinsing, a treatment of removing the developer or rinsing solution adhering on the pattern by a supercritical fluid may be performed.

As for the developer which can be used in the step of performing development by using an organic solvent-containing developer (hereinafter, sometimes referred to as "organic developer") in the pattern forming method of the present invention, a polar solvent such as ketone-based solvent, ester-based solvent, alcohol-based solvent, amide-based solvent and ether-based solvent, or a hydrocarbon-based solvent can be used.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include an alcohol such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include, in addition to the glycol ether-based solvents above, dioxane and tetrahydrofuran.

Examples of the amide-based solvent which can be used include N-methyl-2-pyrrolidone, N,N-dimethylacetamide, N,N-dimethylformamide, hexamethylphosphoric triamide, and 1,3-dimethyl-2-imidazolidinone.

Examples of the hydrocarbon-based solvent include an aromatic hydrocarbon-based solvent such as toluene and xylene, and an aliphatic hydrocarbon-based solvent such as pentane, hexane, octane and decane.

A plurality of these solvents may be mixed, or the solvent may be used by mixing it with a solvent other than those described above or with water. However, in order to sufficiently bring out the effects of the present invention, the percentage of water content in the entire developer is preferably less than 10 mass %, and it is more preferred to contain substantially no water.

In other words, the amount of the organic solvent used in the organic developer is preferably from 90 to 100 mass %, more preferably from 95 to 100 mass %, based on the total amount of the developer.

Above all, the organic developer is preferably a developer containing at least one kind of an organic solvent selected from the group consisting of a ketone-based solvent, an ester-based solvent, an alcohol-based solvent, an amide-based solvent and an ether-based solvent.

The vapor pressure at 20° C. of the organic developer is preferably 5 kPa or less, more preferably 3 kPa or less, still more preferably 2 kPa or less. By setting the vapor pressure of the organic developer to 5 kPa or less, evaporation of the developer on a substrate or in a development cup is suppressed and the temperature uniformity in the wafer plane is enhanced, as a result, the dimensional uniformity in the wafer plane is improved.

Specific examples of the solvent having a vapor pressure of 5 kPa or less include a ketone-based solvent such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone and methyl isobutyl ketone; an ester-based solvent such as butyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol; an ether-based solvent such as tetrahydrofuran; an amide-based solvent such as N-methyl-2-pyrrolidone, N,N-dimethylacetamide and N,N-dimethylformamide; an aromatic hydrocarbon-based solvent such as toluene and xylene; and an aliphatic hydrocarbon-based solvent such as octane and decane.

Specific examples of the solvent having a vapor pressure of 2 kPa or less that is a particularly preferred range include a ketone-based solvent such as 1-octanone, 2-octanone, 1-nonanone, 2-nonanone, 4-heptanone, 2-hexanone, diisobutyl ketone, cyclohexanone, methylcyclohexanone and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate and propyl lactate; an alcohol-based solvent such as n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol; an amide-based solvent such as N-methyl-2-pyrrolidone, N,N-dimethylacetamide and N,N-dimethylformamide; an aromatic hydrocarbon-based solvent such as xylene; and an aliphatic hydrocarbon-based solvent such as octane and decane.

In the organic developer, a surfactant can be added in an appropriate amount, if desired.

The surfactant is not particularly limited but, for example, ionic or nonionic fluorine-containing and/or silicon-containing surfactants can be used. Examples of the fluorine-containing and/or silicon-containing surfactants include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988 and U.S. Pat. Nos. 5,405,720, 5,360,692, 5,529,881, 5,296,330, 5,436,098, 5,576,143, 5,294,511 and 5,824,451. A nonionic surfactant is preferred. The nonionic surfactant is not particularly limited, but use of a fluorine-containing surfactant or a silicon-containing surfactant is more preferred.

The amount of the surfactant used is usually from 0.001 to 5 mass %, preferably from 0.005 to 2 mass %, more preferably from 0.01 to 0.5 mass %, based on the total amount of the developer.

As regards the developing method, for example, a method of dipping the substrate in a bath filled with the developer for a fixed time (dipping method), a method of raising the developer on the substrate surface by the effect of a surface tension and keeping it still for a fixed time, thereby performing the development (puddling method), a method of spraying the developer on the substrate surface (spraying method), and a method of continuously ejecting the developer on the substrate spinning at a constant speed while scanning with a developer ejecting nozzle at a constant rate (dynamic dispense method) may be applied.

In the case where the above-described various developing methods include a step of ejecting the developer toward the resist film from a development nozzle of a developing apparatus, the ejection pressure of the developer ejected (the flow velocity per unit area of the developer ejected) is preferably 2 mL/sec/mm$^2$ or less, more preferably 1.5 mL/sec/mm$^2$ or less, still more preferably 1 mL/sec/mm$^2$ or less. The flow velocity has no particular lower limit but in view of throughput, is preferably 0.2 mL/sec/mm$^2$ or more.

By setting the ejection pressure of the ejected developer to the range above, pattern defects attributable to the resist scum after development can be greatly reduced.

Details of this mechanism are not clearly known, but it is considered that thanks to the ejection pressure in the above-described range, the pressure imposed on the resist film by the developer becomes small and the resist film or resist pattern is prevented from inadvertent chipping or collapse.

Here, the ejection pressure (mL/sec/mm$^2$) of the developer is a value at the outlet of a development nozzle in a developing apparatus.

Examples of the method for adjusting the ejection pressure of the developer include a method of adjusting the ejection pressure by a pump or the like, and a method of supplying the developer from a pressurized tank and adjusting the pressure to change the ejection pressure.

After the step of performing development by using an organic solvent-containing developer, a step of stopping the development by replacing the solvent with another solvent may be practiced.

The pattern forming method preferably includes a step of rinsing the film with a rinsing solution after the step of performing development by using an organic solvent-containing developer.

The rinsing solution used in the rinsing step after the step of performing development by using an organic solvent-containing developer is not particularly limited as long as it does not dissolve the resist pattern, and a solution containing a general organic solvent may be used. As the rinsing solution, a rinsing solution containing at least one kind of an organic solvent selected from the group consisting of a hydrocarbon-based solvent, a ketone-based solvent, an ester-based solvent, an alcohol-based solvent, an amide-based solvent and an ether-based solvent is preferably used.

Specific examples of the hydrocarbon-based solvent, ketone-based solvent, ester-based solvent, alcohol-based solvent, amide-based solvent and ether-based solvent are the same as those described above for the organic solvent-containing developer.

After the step of performing development by using an organic solvent-containing developer, more preferably, a step of rinsing the film by using a rinsing solution containing at least one kind of an organic solvent selected from the group consisting of a ketone-based solvent, an ester-based solvent, an alcohol-based solvent and an amide-based solvent is preformed; still more preferably, a step of rinsing the film by using a rinsing solution containing an alcohol-based solvent or an ester-based solvent is performed; yet still more preferably, a step of rinsing the film by using a rinsing solution containing a monohydric alcohol is performed; and most preferably, a step of rinsing the film by using a rinsing solution containing a monohydric alcohol having a carbon number of 5 or more is performed.

The monohydric alcohol used in the rinsing step includes a linear, branched or cyclic monohydric alcohol, and specific examples of the monohydric alcohol which can be used include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol. As for the particularly preferred monohydric alcohol having a carbon number of 5 or more, 1-hexanol, 2-hexanol, 4-methyl-2-pentanol, 1-pentanol, 3-methyl-1-butanol and the like can be used.

A plurality of these components may be mixed, or the solvent may be used by mixing it with an organic solvent other than those described above.

The percentage of water content in the rinsing solution is preferably 10 mass % or less, more preferably 5 mass % or less, still more preferably 3 mass % or less. By setting the percentage of water content to 10 mass % or less, good development characteristics can be obtained.

The vapor pressure at 20° C. of the rinsing solution used after the step of performing development by using an organic solvent-containing developer is preferably from 0.05 to 5 kPa, more preferably from 0.1 to 5 kPa, and most preferably from 0.12 to 3 kPa. By setting the vapor pressure of the rinsing solution to the range of 0.05 to 5 kPa, the temperature uniformity in the wafer plane is enhanced and moreover, swelling due to permeation of the rinsing solution is suppressed, as a result, the dimensional uniformity in the wafer plane is improved.

The rinsing solution may be also used after adding thereto a surfactant in an appropriate amount.

In the rinsing step, the wafer after development using an organic solvent-containing developer is rinsed using the above-described organic solvent-containing rinsing solution. The method for rinsing treatment is not particularly limited, but examples of the method which can be applied include a method of continuously ejecting the rinsing solution on the substrate spinning at a constant speed (spin coating method), a method of dipping the substrate in a bath filled with the rinsing solution for a fixed time (dipping method), and a method of spraying the rinsing solution on the substrate surface (spraying method). Above all, it is preferred to perform the rinsing treatment by the spin coating method and after the rinsing, remove the rinsing solution from the substrate surface by spinning the substrate at a rotation speed of 2,000 to 4,000 rpm. It is also preferred to include a heating step (Post Bake) after the rinsing step. The developer and rinsing solution remaining between patterns and in the inside of the pattern are removed by the baking. The heating step after the rinsing step is performed at usually from 40 to 160° C., preferably from 70 to 95° C., for usually from 10 seconds to 3 minutes, preferably from 30 to 90 seconds.

The present invention also relates to a method for manufacturing an electronic device, comprising the pattern forming method of the present invention, and an electronic device manufactured by this manufacturing method.

The electronic device of the present invention is suitably mounted on electric/electronic equipment (such as home electronic device, OA•media-related device, optical device and communication device).

EXAMPLES

The mode for carrying out the present invention is described in greater detail below by referring to Examples, but the present invention is limited to these Examples. In the following Synthesis Examples and Examples, the structure of the compound was confirmed by $^1$H-NMR measurement. Also, the molecular weight was confirmed by LC-MS measurement.

Synthesis Example 1

Synthesis of Compound A1

Into a four-neck flack (1,000 ml) equipped with a dropping funnel, a Dimroth condenser, a thermometer and a stirring blade, which was sufficiently dried and purged with nitrogen, resorcinol (22 g, 0.2 mol) produced by Kanto Chemical Co., Inc., 4-isopropylbenzaldehyde (29.6 g, 0.2 mol) produced by Tokyo Chemical Industry Co., Ltd. and dehydrated ethanol (200 ml) were charged under a nitrogen steam to prepare an ethanol solution. This solution was heated to 85° C. in an oil bath with stirring. Subsequently, 75 ml of concentrated hydrochloric acid (35 mass %) was added dropwise over 30 minutes from the dropping funnel, and the resulting solution was continuously stirred at 85° C. for 3 hours. After the completion of the reaction, the reaction solution was allowed to cool and reach room temperature and then cooled in an ice bath. When the solution was left to stand for 1 hour, a pale yellow target crude crystal was produced. This crude crystal was separated by filtration, washed with 500 ml of methanol twice, separated by filtration and vacuum-dried to obtain the target product (hereinafter, referred to as PA-1) (45.1 g, yield: 94%).

Furthermore, in a four-neck flack (1,000 ml) equipped with a dropping funnel, a Dimroth condenser, a thermometer and a stirring blade, which was sufficiently dried and purged with nitrogen, di-tert-butyl dicarbonate (8.7 g, 40 mmol) was added dropwise to a solution containing the synthesized PA-1 (9.6 g, 10 mmol), 4,4'-dimethylaminopyridine (0.1 g, 1 mmol) and acetone under a nitrogen stream. The reaction solution was stirred at room temperature for 1 hour and after the completion of the reaction, the solvent was removed. The obtained solid was purified by column chromatography using a mixed solvent of hexane/ethyl acetate=1/3 (by volume) to obtain 12.5 g of Compound A1 where 50 mol % of the hydrogen atom in the phenolic hydroxyl group was substituted for by a tert-butoxycarbonyl group (hereinafter, sometimes simply referred to as "tBOC group").

Synthesis Example 2

Synthesis of Compound A2

In a four-neck flack (1,000 ml) equipped with a dropping funnel, a Dimroth condenser, a thermometer and a stirring blade, which was sufficiently dried and purged with nitrogen, a 100 ml tetrahydrofuran solution of methyladamantyl bromoacetate (11.4 g, 40 mmol) was added dropwise to a solution containing PA-1 (9.6 g, 10 mmol) synthesized in the same manner as in Synthesis Example 1, potassium carbonate (13.8 g) and 400 ml of tetrahydrofuran under a nitrogen stream. The reaction solution was stirred at room temperature for 1 hour and after the completion of the reaction, the solvent was removed. The obtained solid was purified by column chromatography using a mixed solvent of hexane/ethyl acetate=1/3 (by volume) to obtain 13.1 g of Compound A2 where 50 mol % of the phenolic hydroxyl group was substituted for by a methyladamantyloxycarbonylmethyl group.

Synthesis Example 3

Synthesis of Compound A3

PA-2 was obtained (55.8 g, yield: 96%) in the same manner as in Synthesis Example 1 except for changing 4-isopropylbenzaldehyde to 4-cyclohexylbenzaldehyde and changing resorcinol to pyrogallol at the synthesis of PA-1 in Synthesis Example 1.

The result of LC-MS analysis showed that the structure of the compound obtained had a molecular weight of 1,160 of the target compound. Subsequently, in a four-neck flack (1,000 ml) equipped with a dropping funnel, a Dimroth condenser, a thermometer and a stirring blade, which was sufficiently dried and purged with nitrogen, cyclohexyl vinyl ether (7.5 g, 60 mmol) was added dropwise to a solution containing the synthesized PA-2 (11.6 g, 10 mmol), pyridinium p-toluenesulfonate (2.5 g) and 400 ml of 1,3-dioxolane under a nitrogen steam. The reaction solution was stirred at room temperature for 24 hours and after the completion of the reaction, the solvent was removed. The obtained solid was purified by column chromatography using a mixed solvent of hexane/ethyl acetate=1/3 (by volume) to obtain 28.7 g of Compound A3 where 50 mol % of the phenolic hydroxyl group was substituted for by a cyclohexylethyl group.

Synthesis Example 4

Synthesis of Compound A4

In a four-neck flack (1,000 mL) equipped with a dropping funnel, a Dimroth condenser, a thermometer and a stirring blade, which was sufficiently dried and purged with nitrogen, a 100 ml THF solution of 28.6 g (100 mmol) of methyladamantyl bromoacetate was added dropwise to a solution containing p-hydroxybenzaldehyde (12.2 g/100 mmol), potassium carbonate (13.8 g/100 mmol) and 200 ml of THF under a nitrogen stream. The reaction solution was stirred for 24 hours under reflux and after the completion of the reaction, the solvent was removed. The obtained solid was purified by column chromatography using a mixed solvent of hexane/ethyl acetate=1/3 (by volume) to obtain 29.0 g of PA-4 where the phenolic hydroxyl group was substituted for by a methyladamantyloxycarbonylmethyl group.

Subsequently, into a four-neck flack (1,000 mL) equipped with a dropping funnel, a Dimroth condenser, a thermometer and a stirring blade, which was sufficiently dried and purged with nitrogen, resorcinol (5.5 g, 50 mmol) produced by Kanto Chemical Co., Inc., PA-4 (16.4 g, 50 mol) and ethanol (330 ml) were charged under a nitrogen steam to prepare an ethanol solution. Thereafter, 75 ml of concentrated hydrochloric acid (35%) was added dropwise over 60 minutes from the dropping funnel, and the resulting solution was continuously stirred at room temperature for 6 hours. After the completion of the reaction, the reaction solution was cooled in an ice bath, and a pale yellow target crude crystal was separated by filtration. The crude crystal was washed with 300 ml of distilled water and further with 300 ml of methanol twice, separated by filtration and vacuum-dried to obtain Compound A4 (20.2 g).

Compounds A5 to A9 were synthesized in the same manner as in Synthesis Examples above.

The structural formulae of Compounds A1 to A9 are shown below.

| Compound | Chemical Formula | Molecular Weight |
|---|---|---|
| A1 | 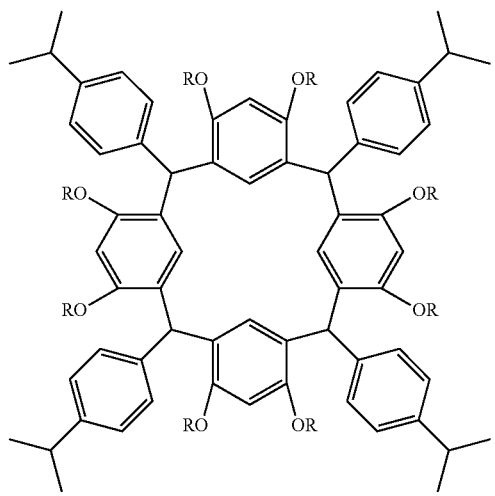 R = H/tBOC = 50/50 mol % | 1362 |
| A2 | 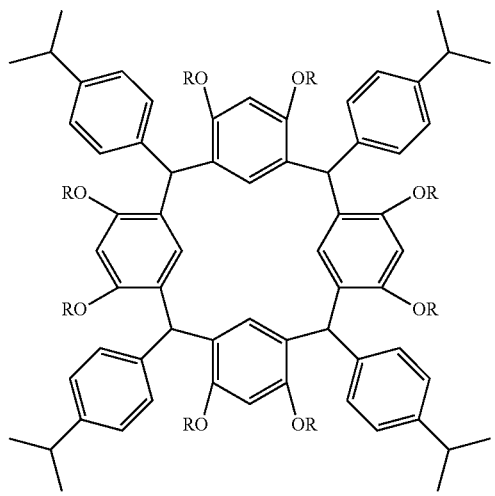 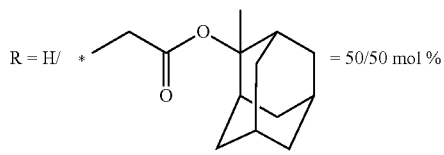 [SMILES: CCC(=O)OC1(C)C2CC3CC(C2)CC1C3] R = H/ * ~~~ = 50/50 mol % | 1786 |

-continued
| Compound | Chemical Formula | Molecular Weight |
|---|---|---|
| A3 | 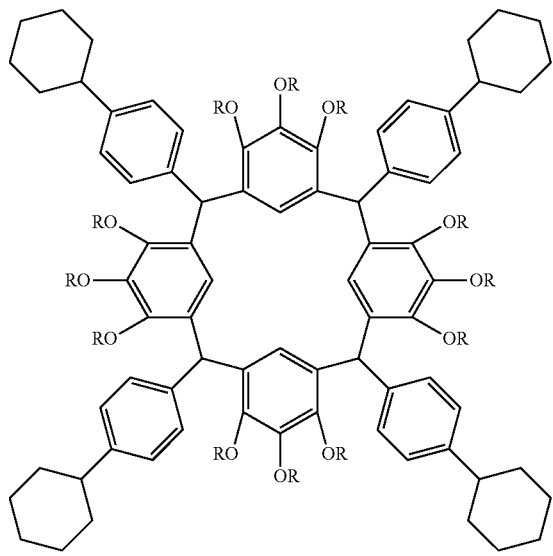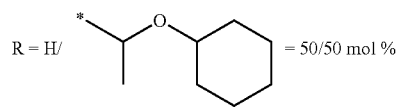 | 1943 |
| A4 | 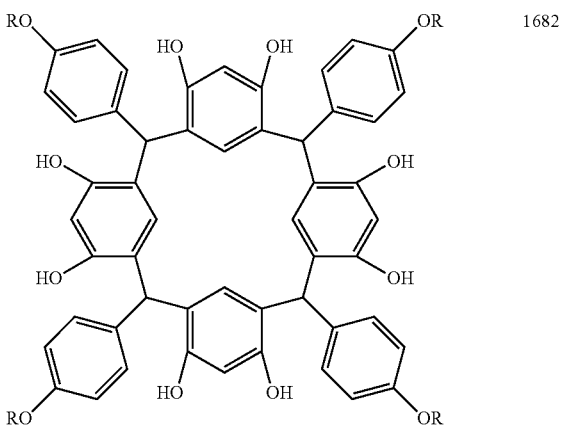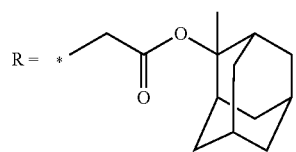 [SMILES: CCC(=O)OC1(C)C2CC3CC(C2)CC1C3] | 1682 |

-continued
| Compound | Chemical Formula | Molecular Weight |
|---|---|---|
| A5 | 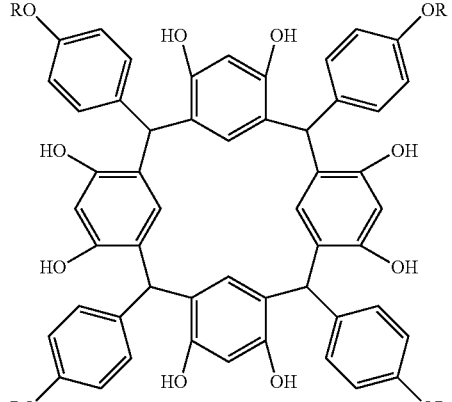 | 1802 |
| A6 |  | 2227 |

-continued
| Compound | Chemical Formula | Molecular Weight |
|---|---|---|
| A7 | 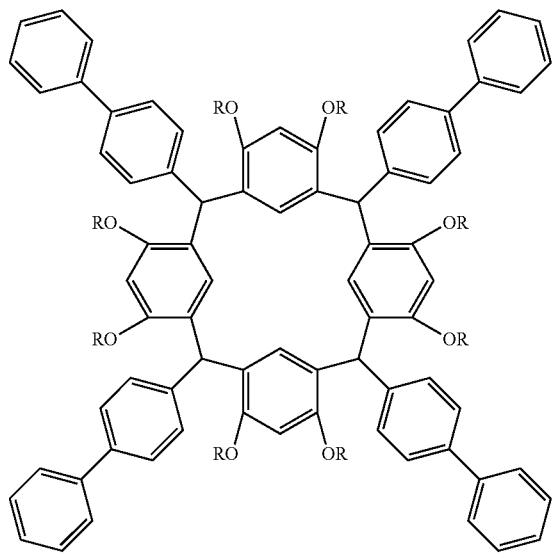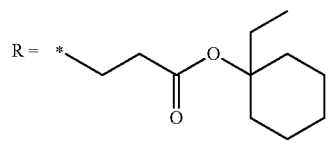 | 2555 |
| A8 | 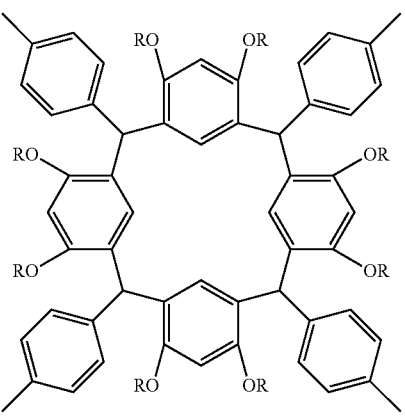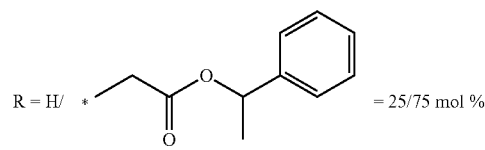 | 1822 |

| Compound | Chemical Formula | Molecular Weight |
|---|---|---|
| A9 | 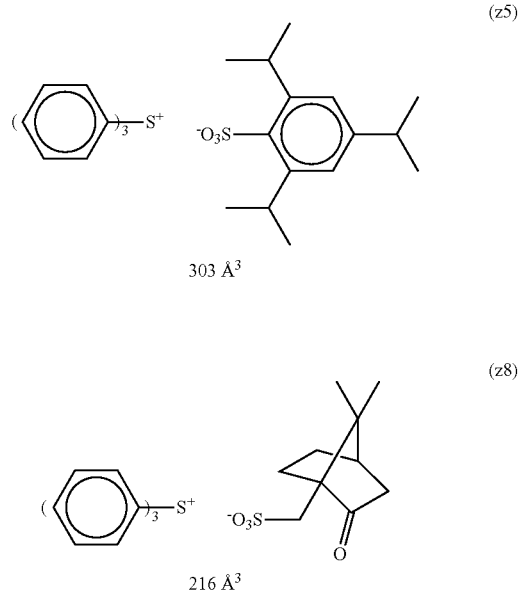 | 2707 |

Also, as a compound for comparison, the following acid-decomposable resin (R1) was synthesized by a known method. The weight average molecular weight (Mw: in terms of polystyrene) and polydispersity (Mw/Mn) of the acid-decomposable resin were calculated by GPC (solvent: THF) measurement. The compositional ratio (molar ratio) was calculated by $^1$H-NMR measurement.

| Compound | Chemical Formula |
|---|---|
| R1 | 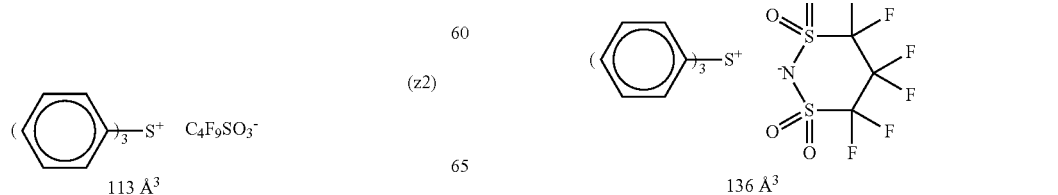 | a/b = 70/30 mol %
Mw = 5500, Polydispersity: 1.1

<Photoacid Generator>

As the photoacid generator, the following compounds were used.

(z2)

$(C_6H_5)_3$-S$^+$  $C_4F_9SO_3^-$

113 Å$^3$ (z5)

303 Å$^3$ (z8)

216 Å$^3$ (z37)

136 Å$^3$

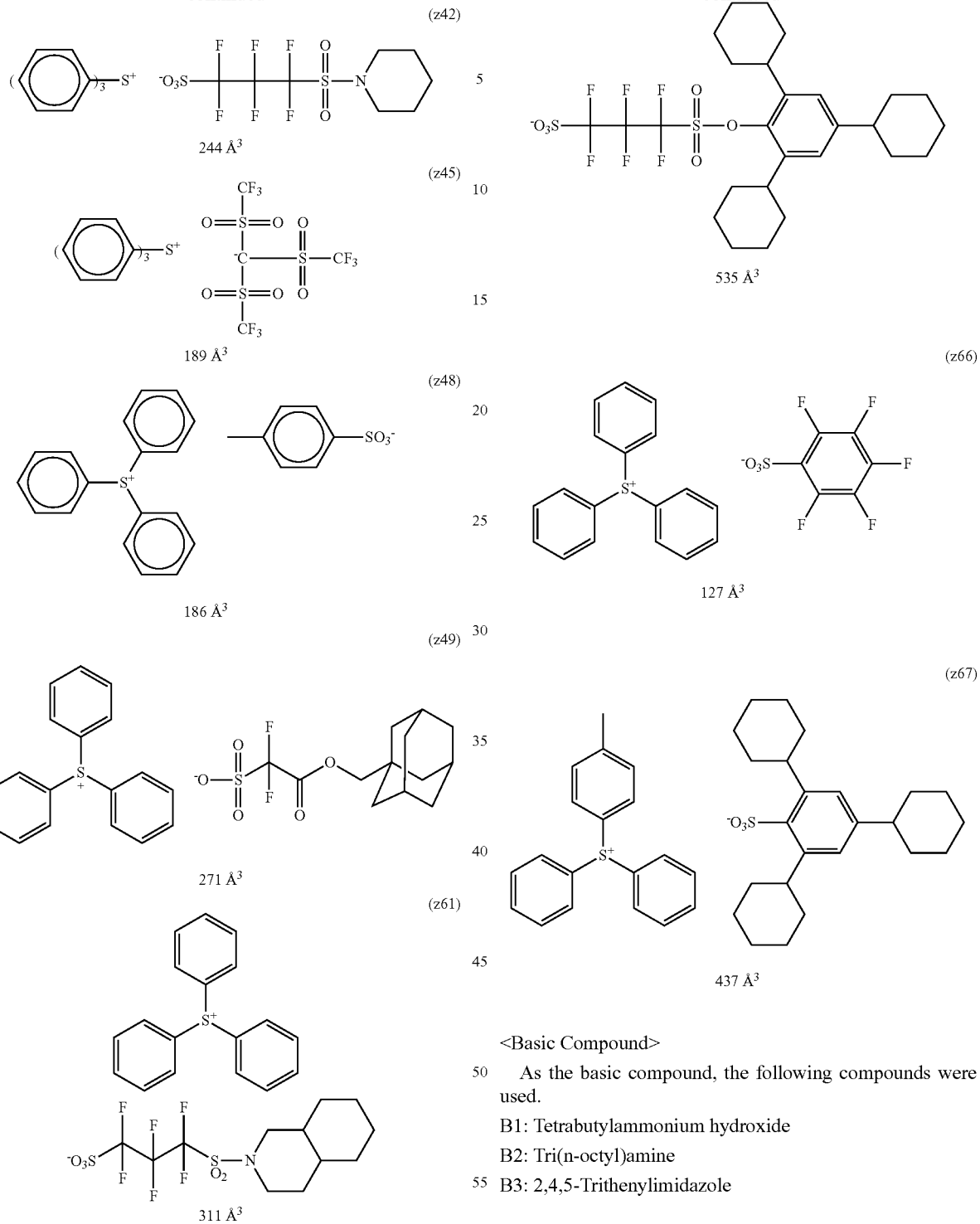
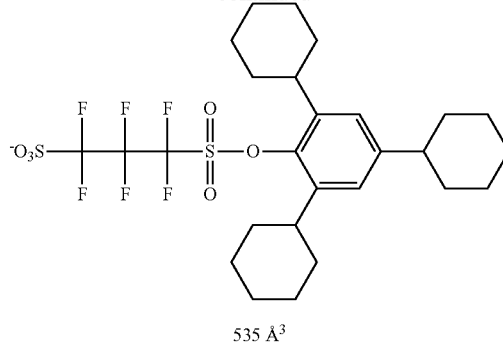
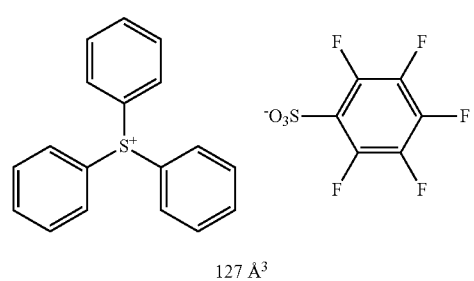
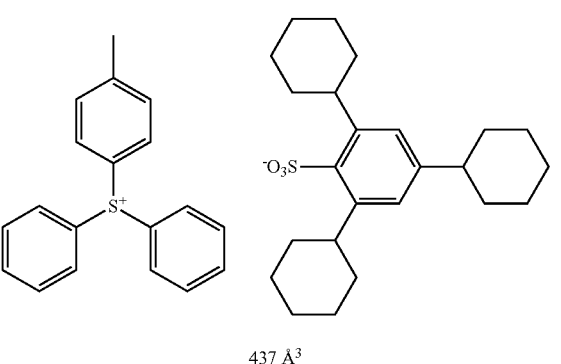
<Basic Compound>
As the basic compound, the following compounds were used.
B1: Tetrabutylammonium hydroxide
B2: Tri(n-octyl)amine
B3: 2,4,5-Trithenylimidazole
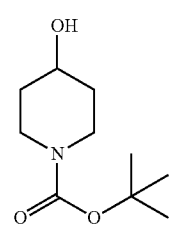

-continued

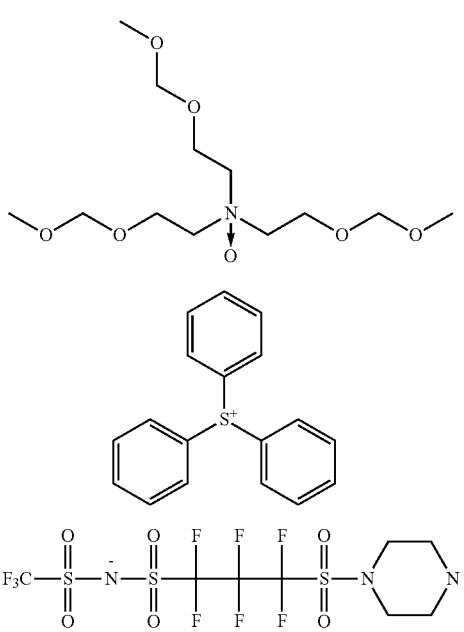

B5

B6

<Surfactant>
As the surfactant, the followings were prepared.
W-1: Megaface F176 (produced by DIC Corp.; fluorine-containing)
W-2: Megaface R08 (produced by DIC Corp.; fluorine- and silicon-containing)
W-3: Polysiloxane Polymer KP-341 (produced by Shin-Etsu Chemical Co., Ltd.; silicon-containing)
W-4: Troysol S-366 (produced by Troy Chemical)
W-5: KH-20 (produced by Asahi Glass Co., Ltd.)
W-6: PolyFox PF-6320 (produced by OMNOVA Solutions Inc., fluorine-containing)
<Solvent>
As the solvent, the followings were prepared.
(Group a)
SL-1: Propylene glycol monomethyl ether acetate (PGMEA)
SL-2: Propylene glycol monomethyl ether propionate
SL-3: 2-Heptanone
(Group b)
SL-4: Ethyl lactate
SL-5: Propylene glycol monomethyl ether (PGME)
SL-6: Cyclohexanone
(Group c)
SL-7: γ-Butyrolactone
SL-8: Propylene carbonate
<Developer>
As the developer, the followings were prepared.
SG-1: Butyl acetate
SG-2: Methyl amyl ketone
SG-3: Ethyl-3-ethoxypropionate
SG-4: Pentyl acetate
SG-5: Isopentyl acetate
SG-6: Propylene glycol monomethyl ether acetate (PGMEA)
SG-7: Cyclohexanone
<Rinsing Solution>
As the rinsing solution, the followings were used.
SR-1: 4-Methyl-2-pentanol
SR-2: 1-Hexanol
SR-3: Butyl acetate
SR-4: Methyl amyl ketone
SR-5: Ethyl-3-ethoxypropionate Examples 1 to 12 and Comparative Examples 1 and 2

Evaluation by EB Exposure (Preparation of Resist Composition)

The components shown in Table 1 below were dissolved in the solvent shown in the same Table to give a solid content of 2.8 mass %, and the obtained solution was filtered through a polyethylene filter having a pore size of 0.03 µm to prepare an actinic ray-sensitive or radiation-sensitive composition (resist composition).

(Formation of Resist Film)

The prepared resist composition solution was uniformly coated on a silicon substrate by a spin coater and baked (PB: Prebake) at 100° C. over 60 seconds to form a resist film having a thickness of 60 nm.

(Production of Resist Pattern (EB Exposure))

The resist film was patternwise irradiated using an electron beam lithography system (ELS-7500, manufactured by Elionix Inc., accelerating voltage: 50 keV). After the irradiation, the resist film was heated (PEB: Post Exposure Bake) on a hot plate at 110° C. for 60 seconds, developed by puddling the organic solvent-based developer shown in the Table below for 30 seconds, and then rinsed by puddling the rinsing solution shown in the Table below for 30 seconds while rotating the wafer at a rotation speed of 1,000 rpm. Subsequently, the wafer was rotated at a rotation speed of 4,000 rpm for 30 seconds, whereby a resist pattern was obtained.

However, in Comparative Example 2, the pattern formation was performed using an aqueous 2.38 mass % tetramethylammonium hydroxide (TMAH) solution as the developer and using water as the rinsing solution.

(Evaluation of Resist Pattern)

The obtained pattern was evaluated for the resolution, line edge roughness (LER) and dry etching resistance by the following methods.

[Resolution (LS)]

The cross-sectional profile of the obtained pattern was observed using a scanning electron microscope (S-4300, manufactured by Hitachi, Ltd.). The optimum exposure dose (dose of electron beam irradiation) when resolving a resist pattern with a line width of 50 nm (line:space=1:1) was taken as the sensitivity ($E_{opt}$) (µC/cm$^2$). The limiting resolution (the minimum line width below which the line and the space (line:space=1:1) were not separated and resolved) at the optimum exposure dose ($E_{opt}$) determined above was taken as the LS resolution (nm). As the value obtained is smaller, the resolution is more excellent and this is better.

[Line Edge Roughness (LER)]

A resist pattern having a line width of 50 nm (line:space=1:1) was formed with the irradiation dose (dose of electron beam irradiation) giving the sensitivity above. At arbitrary 30 points included in the longitudinal 50 µm region, the distance from the reference line where the edge should be present was measured using a scanning electron microscope (S-9220, manufactured by Hitachi, Ltd.). The standard deviation of the measured distances was determined, and 3σ was computed. A smaller value indicates better performance.

[Dry Etching Resistance]

A resist film where a resist pattern having a line width of 50 nm (line:space=1:1) was formed with the irradiation dose (dose of electron beam irradiation) giving the sensitivity above was subjected to dry etching for 30 seconds by using an Ar/C$_4$F$_6$/O$_2$ gas (a mixed gas in a volume ratio of 100/4/2) in HITACHI U-621. Thereafter, the residual resist film ratio was measured and used as an indicator of dry etching resistance.

A (very good): A residual film ratio of 95% or more.
B (good): From 90% to less than 95%.
C (bad): Less than 90%.

The evaluation results are shown in Table 1.

a spin coater and baked (PB: Prebake) at 100° C. over 60 seconds to form a resist film having a thickness of 60 nm.
(Production of Resist Pattern (EUV Exposure))

The resist film was exposed to EUV light (wavelength: 13.5 nm) through a reflective mask having a 1:1 line-and-space pattern with a line width of 50 nm by changing the

TABLE 1

| Example | Compound (A) | (g) | Photoacid Generator | (g) | Basic Compound | (g) | Solvent | Mass Ratio | Surfactant |
|---|---|---|---|---|---|---|---|---|---|
| Example 1 | A1 | 6 | z48 | 1.2 | B1 | 0.02 | SL-1/SL-5 | 60/40 | W-1 |
| Example 2 | A2 | 6 | z42 | 1.2 | B2 | 0.02 | SL-1/SL-2 | 90/10 | W-2 |
| Example 3 | A3 | 6 | z5 | 1.2 | B3 | 0.02 | SL-1/SL-3 | 80/20 | W-3 |
| Example 4 | A4 | 6 | z45 | 1.2 | B4 | 0.02 | SL-1/SL-4 | 90/10 | — |
| Example 5 | A5 | 6 | z8 | 1.2 | B5 | 0.02 | SL-1/SL-5 | 70/30 | W-4 |
| Example 6 | A6 | 6 | z37 | 1.2 | B1 | 0.02 | SL-1 | 100 | W-5 |
| Example 7 | A6 | 6 | z63/z2 | 1.0/0.2 | B2 | 0.02 | SL-1/SL-5 | 60/40 | — |
| Example 8 | A7 | 6 | z67 | 1.2 | B3 | 0.02 | SL-1/SL-6 | 80/20 | W-6 |
| Example 9 | A8 | 6 | z49 | 1.2 | B4 | 0.02 | SL-1/SL-7 | 95/5 | — |
| Example 10 | A9 | 6 | z61 | 1.2 | B5 | 0.02 | SL-1/SL-5 | 60/40 | W-1 |
| Example 11 | A9 | 6 | z63 | 1.2 | B1/B6 | 0.01/0.01 | SL-1/SL-3 | 80/20 | — |
| Example 12 | A4/A5 | 3/3 | z66 | 1.2 | B2 | 0.02 | SL-1/SL-8 | 95/5 | — |
| Comparative Example 1 | Resin R1 | 6 | z48 | 1.2 | B1 | 0.02 | SL-1/SL-5 | 60/40 | W-1 |
| Comparative Example 2 (Alkali development) | A1 | 6 | z48 | 1.2 | B1 | 0.02 | SL-1/SL-5 | 60/40 | W-1 |

| Example | (g) | Developer | Mass Ratio | Rinsing Solution | Mass Ratio | LS Resolution (nm) | LER (nm) | Dry Etching Resistance |
|---|---|---|---|---|---|---|---|---|
| Example 1 | 0.001 | SG-1 | 100 | SR-1 | 100 | 35 | 3.6 | A |
| Example 2 | 0.001 | SG-1 | 100 | SR-1 | 100 | 35 | 3.7 | A |
| Example 3 | 0.001 | SG-1/SG-4 | 90/10 | SR-2 | 100 | 35 | 3.8 | A |
| Example 4 | — | SG-1 | 100 | SR-1 | 100 | 35 | 3.6 | A |
| Example 5 | 0.001 | SG-1 | 100 | SR-1 | 100 | 35 | 3.6 | A |
| Example 6 | 0.001 | SG-1/SG-3 | 90/10 | SR-3 | 100 | 35 | 3.7 | A |
| Example 7 | — | SG-1/SG-7 | 95/5 | SR-1 | 100 | 38 | 3.9 | A |
| Example 8 | 0.001 | SG-1/SG-6 | 95/5 | SR-1 | 100 | 35 | 3.8 | A |
| Example 9 | — | SG-1 | 100 | SR-1 | 100 | 35 | 3.7 | A |
| Example 10 | 0.001 | SG-2 | 100 | SR-4 | 100 | 35 | 3.6 | A |
| Example 11 | — | SG-1 | 100 | SR-1 | 100 | 35 | 3.6 | A |
| Example 12 | — | SG-1/SG-5 | 70/30 | SR-5 | 100 | 38 | 4.0 | A |
| Comparative Example 1 | 0.001 | SG-1 | 100 | SR-1 | 100 | Pattern could not be formed. | | |
| Comparative Example 2 (Alkali development) | 0.001 | Aqueous 2.38 mass % TMAH solution | 100 | water | 100 | 50 | 6.9 | A |

It is seen from the results shown in Table 1 that according to the pattern forming method of the present invention, at the time of forming a pattern having an ultrafine line part, all of high resolution, small line edge roughness (LER) and good dry etching resistance can be satisfied at the same time.

Examples 13 to 24 and Comparative Examples 3 and 4

Evaluation by EUV Exposure (Preparation of Resist Composition)

The components shown in Table 2 below were dissolved in the solvent shown in the same Table to give a solid content of 2.8 mass %, and the obtained solution was filtered through a polyethylene filter having a pore size of 0.03 μm to prepare an actinic ray-sensitive or radiation-sensitive composition (resist composition).

(Formation of Resist Film)

The prepared resist composition solution was uniformly coated on a hexamethyldisilazane-treated silicon substrate by exposure dose in steps of 0.1 mJ/cm$^2$ in the range of 0 to 20.0 mJ/cm$^2$, baked at 110° C. for 90 seconds, developed by puddling the organic solvent-based developer shown in the Table below for 30 seconds, and then rinsed by puddling the rinsing solution shown in the Table below for 30 seconds while rotating the wafer at a rotation speed of 1,000 rpm. Subsequently, the wafer was rotated at a rotation speed of 4,000 rpm for 30 seconds, whereby a resist pattern was obtained.

However, in Comparative Example 4, the pattern formation was performed using an aqueous 2.38 mass % tetramethylammonium hydroxide (TMAH) solution as the developer and using water as the rinsing solution.

(Evaluation of Resist Pattern)

The obtained pattern was evaluated for the resolution, line edge roughness (LER) and dry etching resistance by the following methods.

[Resolution (LS)]

The cross-sectional profile of the obtained pattern was observed using a scanning electron microscope (S-4300, manufactured by Hitachi, Ltd.). The optimum exposure dose when resolving a resist pattern with a line width of 50 nm (line:space=1:1) was taken as the sensitivity ($E_{opt}$) (mJ/cm$^2$). The limiting resolution (the minimum line width below which the line and the space (line:space=1:1) were not separated and resolved) at the optimum exposure dose ($E_{opt}$) determined was taken as the LS resolution (nm). As the value volume ratio of 100/4/2) in HITACHI U-621. Thereafter, the residual resist film ratio was measured and used as an indicator of dry etching resistance.

A (very good): A residual film ratio of 95% or more.
B (good): From 90% to less than 95%.
C (bad): Less than 90%.

The evaluation results are shown in Table 2.

TABLE 2

| Example | Compound (A) | (g) | Photoacid Generator | (g) | Basic Compound | (g) | Solvent | Mass Ratio | Surfactant | (g) | Developer | Mass Ratio | Rinsing Solution | Mass Ratio | LS Resolution (nm) | LER (nm) | Dry Etching Resistance |
|---|---|---|---|---|---|---|---|---|---|---|---|---|---|---|---|---|---|
| Example 13 | A1 | 6 | z48 | 1.2 | B1 | 0.02 | SL-1/SL-5 | 60/40 | W-1 | 0.001 | SG-1 | 100 | SR-1 | 100 | 30 | 3.5 | A |
| Example 14 | A2 | 6 | z42 | 1.2 | B2 | 0.02 | SL-1/SL-2 | 90/10 | W-2 | 0.001 | SG-1 | 100 | SR-1 | 100 | 30 | 3.6 | A |
| Example 15 | A3 | 6 | z5 | 1.2 | B3 | 0.02 | SL-1/SL-3 | 80/20 | W-3 | 0.001 | SG-1/SG-4 | 90/10 | SR-2 | 100 | 30 | 3.7 | A |
| Example 16 | A4 | 6 | z45 | 1.2 | B4 | 0.02 | SL-1/SL-4 | 90/10 | — | — | SG-1 | 100 | SR-1 | 100 | 30 | 3.6 | A |
| Example 17 | A5 | 6 | z8 | 1.2 | B5 | 0.02 | SL-1/SL-5 | 70/30 | W-4 | 0.001 | SG-1 | 100 | SR-1 | 100 | 30 | 3.6 | A |
| Example 18 | A6 | 6 | z37 | 1.2 | B1 | 0.02 | SL-1 | 100 | W-5 | 0.001 | SG-1/SG-3 | 90/10 | SR-3 | 100 | 30 | 3.6 | A |
| Example 19 | A6 | 6 | z63/z2 | 1.0/0.2 | B2 | 0.02 | SL-1/SL-5 | 60/40 | — | — | SG-1/SG-7 | 95/5 | SR-1 | 100 | 33 | 3.7 | A |
| Example 20 | A7 | 6 | z67 | 1.2 | B3 | 0.02 | SL-1/SL-6 | 80/20 | W-6 | 0.001 | SG-1/SG-6 | 95/5 | SR-1 | 100 | 30 | 3.7 | A |
| Example 21 | A8 | 6 | z49 | 1.2 | B4 | 0.02 | SL-1/SL-7 | 95/5 | — | — | SG-1 | 100 | SR-1 | 100 | 30 | 3.6 | A |
| Example 22 | A9 | 6 | z61 | 1.2 | B5 | 0.02 | SL-1/SL-5 | 60/40 | W-1 | 0.001 | SG-2 | 100 | SR-4 | 100 | 30 | 3.5 | A |
| Example 23 | A9 | 6 | z63 | 1.2 | B1/B6 | 0.01/0.01 | SL-1/SL-3 | 80/20 | — | — | SG-1 | 100 | SR-1 | 100 | 30 | 3.5 | A |
| Example 24 | A4/A5 | 3/3 | z66 | 1.2 | B2 | 0.02 | SL-1/SL-8 | 95/5 | — | — | SG-1/SG-5 | 70/30 | SR-5 | 100 | 33 | 3.8 | A |
| Comparative Example 3 | Resin R1 | 6 | z48 | 1.2 | B1 | 0.02 | SL-1/SL-5 | 60/40 | W-1 | 0.001 | SG-1 | 100 | SR-1 | 100 | Pattern could not be formed. | | |
| Comparative Example 4 (Alkali development) | A1 | 6 | z48 | 1.2 | B1 | 0.02 | SL-1/SL-5 | 60/40 | W-1 | 0.001 | Aqueous 2.38 mass % TMAH solution | 100 | water | 100 | 45 | 6.5 | A | obtained is smaller, the resolution is more excellent and this is better.

[Line Edge Roughness (LER)]

A resist pattern having a line width of 50 nm (line:space=1:1) was formed with the optimum exposure dose giving the sensitivity above. At arbitrary 30 points included in the longitudinal 50 μm region, the distance from the reference line where the edge should be present was measured using a scanning electron microscope (S-9220, manufactured by Hitachi, Ltd.). The standard deviation of the measured distances was determined, and 3σ was computed. A smaller value indicates better performance.

[Dry Etching Resistance]

A resist film where a resist pattern having a line width of 50 nm (line:space=1:1) was formed with the optimum exposure dose giving the sensitivity above was subjected to dry etching for 30 seconds by using an Ar/C$_4$F$_6$/O$_2$ gas (a mixed gas in a It is seen from the results shown in Table 2 that according to the pattern forming method of the present invention, at the time of forming a pattern having an ultrafine line part, all of high resolution, small line edge roughness (LER) and good dry etching resistance can be satisfied at the same time.

INDUSTRIAL APPLICABILITY

According to the present invention, a pattern forming method capable of forming a pattern satisfying high resolution, small line edge roughness (LER) and good dry etching resistance all at the same time in forming a pattern having an ultrafine line part (for example, with a line width of 50 nm or less), an actinic ray-sensitive or radiation-sensitive composition for use in the pattern forming method, a resist film, a manufacturing method of an electronic device using the same, and an electronic device can be provided.

This application is based on a Japanese patent application filed on Mar. 27, 2012 (Japanese Patent Application No. 2012-72541), and the contents thereof are incorporated herein by reference.

The invention claimed is:

1. A pattern forming method comprising:

(i) a step of forming a film by using an actinic ray-sensitive or radiation-sensitive composition containing (A) a non-polymeric acid-decomposable compound having an aromatic ring and a molecular weight of 500 to 5,000 and (B) a compound capable of generating an acid upon irradiation with an actinic ray or radiation, wherein the compound (A) is a compound represented by the following formula (1):

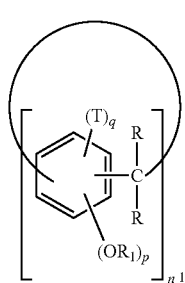

(1)

wherein each R independently represents a hydrogen atom or a substituent selected from an alkyl group, a cycloalkyl group, an aryl group, an aralkyl group, an acyl group, an alkoxyl group, a cyano group, a nitro group, a hydroxyl group, a heterocyclic group, a carboxyl group, an alkylsilyl group, and a group having a structure capable of decomposing by the action of an acid to produce a polar group, and each R in the compound (A) may be the same as or different from every other R;

$OR_1$ represents a hydroxyl group or a group having a structure capable of decomposing by the action of an acid to produce a polar group, and each $OR_1$ in the compound (A) may be same as or different from every other $OR_1$, with the proviso that at least one of the plurality of $OR_1$s and the plurality of Rs is a group having a structure capable of decomposing by the action of an acid to produce a polar group;

T represents a hydrogen atom or a substituent selected from an alkyl group, a cycloalkyl group, an aryl group, an aralkyl group, an acyl group, an alkoxyl group, a cyano group, a nitro group, a hydroxyl group, a heterocyclic group, a halogen atom, a carboxyl group, and an alkylsilyl group, and when a plurality of Ts are present, each T may be the same as or different from every other T;

p represents an integer of 1 to 4;

q represents an integer represented by (4-p);

n1 represents an integer of 3 or more;

n1 ps may be the same value or different values; and n1 qs may be the same value or different values, (ii) a step of exposing the film, and (iii) a step of performing development by using an organic solvent-containing developer to form a negative pattern, wherein the developer comprises at least one kind of an organic solvent selected from the group consisting of a ketone-based solvent, an ester-based solvent, an alcohol-based solvent and an amide-based solvent.

2. The pattern forming method as claimed in claim 1, wherein the compound (A) is a compound represented by the following formula (2):

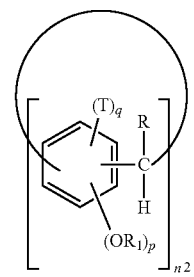

(2)

wherein $OR_1$, R, T, p and q have the same meanings as $OR_1$, R, T, p and q in formula (1), respectively, and each $OR_1$, R or T in the compound (A) may be the same as or different from every other $OR_1$, R or T, with the proviso that at least one of the plurality of $OR_1$s and the plurality of Rs is a group having a structure capable of decomposing by the action of an acid to produce a polar group;

n2 represents an integer of 3 to 8;

n2 ps may be the same value or different values; and n2 qs may be the same value or different values.

3. The pattern forming method as claimed in claim 2, wherein the compound (A) is a compound represented by the following formula (3):

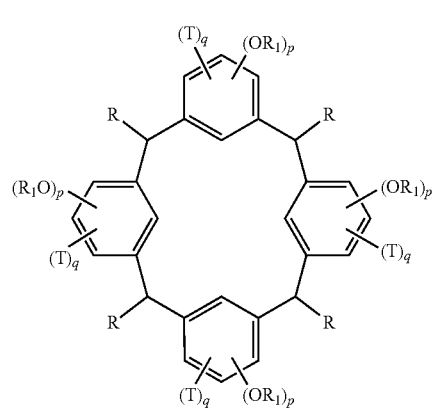

(3)

wherein $OR_1$, R, T, p and q have the same meanings as $OR_1$, R, T, p and q in formula (2), respectively, and each $OR_1$, R or T in the compound (A) may be the same as or different from every other $OR_1$, R or T, with the proviso that at least one of the plurality of $OR_1$s and the plurality of Rs is a group having a structure capable of decomposing by the action of an acid to produce a polar group;

four ps may be the same value or different values; and four qs may be the same value or different values.

4. The pattern forming method as claimed in claim 3, wherein the compound (A) is a compound represented by the following formula (4):

(4)

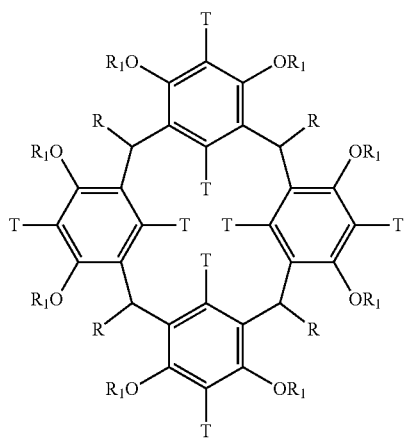

wherein $OR_1$, R and T have the same meanings as $OR_1$, R and T in formula (3), respectively, and each $OR_1$, R or T in the compound (A) may be the same as or different from every other $OR_1$, R or T, with the proviso that at least one of the plurality of $OR_1$s and the plurality of Rs is a group having a structure capable of decomposing by the action of an acid to produce a polar group.

5. The pattern forming method as claimed in claim 1,
wherein at least one R in formula (1) is an aryl group represented by the following formula (5):

(5)

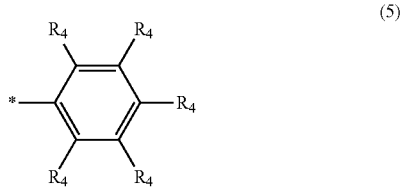

wherein each $R_4$ independently represents a hydrogen atom or a substituent,
with the proviso that at least one of the plurality of $OR_1$s and the plurality of $R_4$s in the compound (A) is a group having a structure capable of decomposing by the action of an acid to produce a polar group.

6. The pattern forming method as claimed in claim 1,
wherein the exposure in the step (ii) is exposure to an electron beam or an extreme-ultraviolet ray (EUV light).

7. The pattern forming method as claimed in claim 1, further comprising:
(iv) a step of performing rinsing by using an organic solvent-containing rinsing solution.

8. The pattern forming method as claimed in claim 1,
wherein the developer comprises at least one kind of an organic solvent selected from a ketone-based solvent, an ester-based solvent and an amide-based solvent.

9. The pattern forming method as claimed in claim 1,
wherein the developer comprises an ester-based solvent.

10. The pattern forming method as claimed in claim 9,
wherein the ester-based solvent is butyl acetate, pentyl acetate or isopentyl acetate.

11. An actinic ray-sensitive or radiation-sensitive composition containing:
(A) a non-polymeric acid-decomposable compound having an aromatic ring and a molecular weight of 500 to 5,000 and (B) a compound capable of generating an acid upon irradiation with an actinic ray or radiation,
wherein the compound (A) is a compound represented by the following formula (1):

(1)

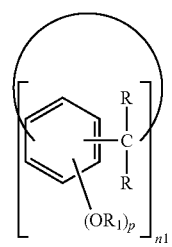

wherein each R independently represents a hydrogen atom or a substituent selected from an alkyl group, a cycloalkyl group, an aryl group, an aralkyl group, an acyl group, an alkoxyl group, a cyano group, a nitro group, a hydroxyl group, a heterocyclic group, a carboxyl group, an alkylsilyl group, and a group having a structure capable of decomposing by the action of an acid to produce a polar group, and each R in the compound (A) may be the same as or different from every other R;
the aryl group represented by R in formula (1) is represented by the following formula (5), wherein each $R_4$ independently represents a hydrogen atom or a substituent selected from an alkyl group, a cycloalkyl group, an aryl group, an aralkyl group, an acyl group, an alkoxy group, a cyano group, a nitro group, a heterocyclic group, a halogen atom, a carboxyl group, and an alkylsilyl group:

(5)

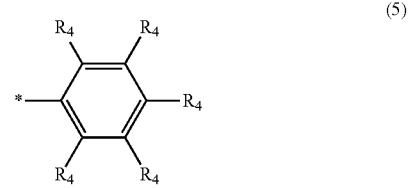

$OR_1$ represents a hydroxyl group or a group having a structure capable of decomposing by the action of an acid to produce a polar group, and each $OR_1$ in the compound (A) may be same as or different from every other $OR_1$, with the proviso that at least one of the plurality of $OR_1$s and the plurality of Rs is a group having a structure capable of decomposing by the action of an acid to produce a polar group;
T represents a hydrogen atom or a substituent selected from an alkyl group, a cycloalkyl group, an aryl group, an aralkyl group, an acyl group, an alkoxyl group, a cyano group, a nitro group, a hydroxyl group, a heterocyclic group, a halogen atom, a carboxyl group, and an alkylsilyl group, and when a plurality of Ts are present, each T may be the same as or different from every other T;
p represents an integer of 1 to 4;
q represents an integer represented by (4-p);
n1 represents an integer of 3 or more;
n1 ps may be the same value or different values; and
n1 qs may be the same value or different values.

12. The actinic ray-sensitive or radiation-sensitive composition according to claim 11, wherein the compound (A) is a compound represented by the following formula (2):

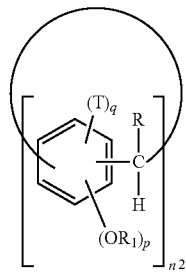

(2)

wherein $OR_1$, R, T, p and q have the same meanings as $OR_1$, R, T, p and q in formula (1), respectively, and each $OR_1$, R or T in the compound (A) may be the same as or different from every other $OR_1$, R or T, with the proviso that at least one of the plurality of $OR_1$s and the plurality of Rs is a group having a structure capable of decomposing by the action of an acid to produce a polar group;

n2 represents an integer of 3 to 8;

n2 ps may be the same value or different values; and n2 qs may be the same value or different values.

13. The actinic ray-sensitive or radiation-sensitive composition according to claim 12, wherein the compound (A) is a compound represented by the following formula (3):

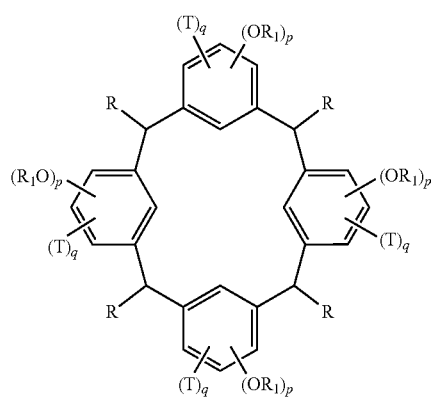

(3)

wherein $OR_1$, R, T, p and q have the same meanings as $OR_1$, R, T, p and q in formula (2), respectively, and each $OR_1$, R or T in the compound (A) may be the same as or different from every other $OR_1$, R or T, with the proviso that at least one of the plurality of $OR_1$S and the plurality of Rs is a group having a structure capable of decomposing by the action of an acid to produce a polar group;

four ps may be the same value or different values; and four qs may be the same value or different values.

14. The actinic ray-sensitive or radiation-sensitive composition according to claim 13, wherein the compound (A) is a compound represented by the following formula (4):

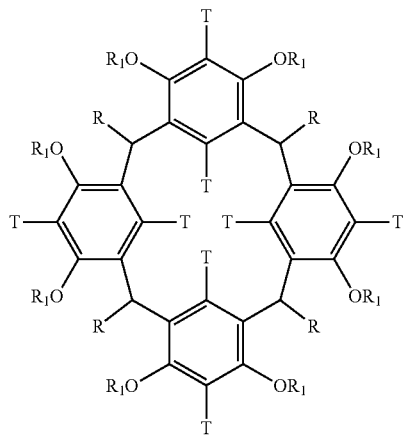

(4)

wherein $OR_1$, R and T have the same meanings as $OR_1$, R and T in formula (3), respectively, and each $OR_1$, R or T in the compound (A) may be the same as or different from every other $OR_1$, R or T, with the proviso that at least one of the plurality of $OR_1$S and the plurality of Rs is a group having a structure capable of decomposing by the action of an acid to produce a polar group.

15. The actinic ray-sensitive or radiation-sensitive composition according to claim 11, wherein at least one R in formula (1) is an aryl group represented by formula (5),
with the proviso that at least one of the plurality of $OR_1$s and the plurality of $R_4$s in the compound (A) is a group having a structure capable of decomposing by the action of an acid to produce a polar group.

16. A resist formed of the actinic ray-sensitive or radiation-sensitive composition claimed in claim 11.

17. An actinic ray-sensitive or radiation-sensitive composition containing:
(A) a non-polymeric acid-decomposable compound having an aromatic ring and a molecular weight of 500 to 5,000 and
(B) a compound capable of generating an acid upon irradiation with an actinic ray or radiation,
wherein the compound (A) is a compound represented by the following formula (1):

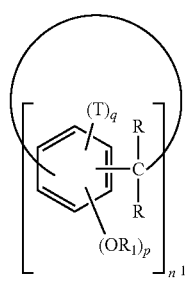

(1)

wherein each R independently represents a hydrogen atom or a substituent selected from an alkyl group, a cycloalkyl group, an aryl group, an aralkyl group, an acyl group, an alkoxyl group, a cyano group, a nitro group, a hydroxyl group, a heterocyclic group, a carboxyl group, an alkylsilyl group, and a group having a structure capable of decomposing by the action of an acid to produce a polar group, and each R in the compound (A) may be the same as or different from every other R;

OR₁ represents a group having a structure capable of decomposing by the action of an acid to produce a polar group, R₁ in OR₁ represents a substituted methyl group, a 1-substituted ethyl group, a 1-substituted-n-propyl group, a 1-branched alkyl group, a silyl group, a 1-substituted alkoxymethyl group, a cyclic ether group, or an alkoxycarbonylalkyl group, and each OR₁ in the compound (A) may be same as or different from every other OR₁;

T represents a hydrogen atom or a substituent selected from an alkyl group, a cycloalkyl group, an aryl group, an aralkyl group, an acyl group, an alkoxyl group, a cyano group, a nitro group, a hydroxyl group, a heterocyclic group, a halogen atom, a carboxyl group, and an alkylsilyl group, and when a plurality of Ts are present, each T may be the same as or different from every other T;

p represents an integer of 1 to 4;

q represents an integer represented by (4-p);

n1 represents an integer of 3 or more;

n1 ps may be the same value or different values; and n1 qs may be the same value or different values.

18. The actinic ray-sensitive or radiation-sensitive composition according to claim 17, wherein $R_1$ in formula (1) represents an alkoxycarbonylalkyl group.

19. The actinic ray-sensitive or radiation-sensitive composition according to claim 17, wherein the compound (A) is a compound represented by the following formula (2):

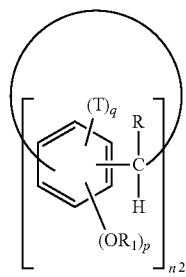

(2)

wherein OR₁, R, T, p and q have the same meanings as OR₁, R, T, p and q in formula (1), respectively, and each OR₁, R or T in the compound (A) may be the same as or different from every other OR₁, R or T;

n2 represents an integer of 3 to 8;

n2 ps may be the same value or different values; and n2 qs may be the same value or different values.

20. The actinic ray-sensitive or radiation-sensitive composition according to claim 19, wherein the compound (A) is a compound represented by the following formula (3):

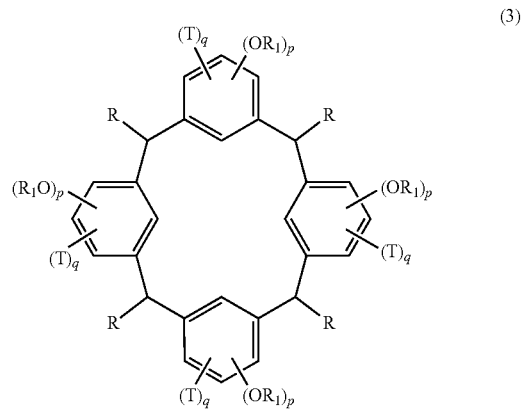

(3)

wherein OR₁, R, T, p and q have the same meanings as OR₁, R, T, p and q in formula (2), respectively, and each OR₁, R or T in the compound (A) may be the same as or different from every other OR₁, R or T four ps may be the same value or different values; and four qs may be the same value or different values.

21. The actinic ray-sensitive or radiation-sensitive composition according to claim 20, wherein the compound (A) is a compound represented by the following formula (4):

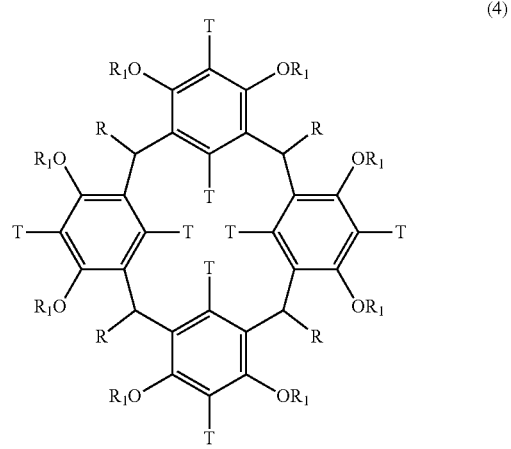

(4)

wherein OR₁, R and T have the same meanings as OR₁, R and T in formula (3), respectively, and each OR₁, R or T in the compound (A) may be the same as or different from every other OR₁, R or T.

22. The actinic ray-sensitive or radiation-sensitive composition according to claim 17, wherein at least one R in formula (1) is an aryl group represented by the following formula (5):

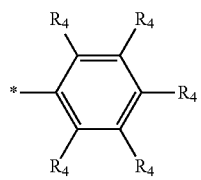

(5)

wherein each $R_4$ independently represents a hydrogen atom or a substituent.

* * * * *